United States Patent
Wang et al.

(10) Patent No.: US 9,422,311 B2
(45) Date of Patent: *Aug. 23, 2016

(54) COMPOUNDS FOR THE TREATMENT OF HEPATITIS C

(71) Applicant: Bristol-Myers Squibb Company, Princeton, NJ (US)

(72) Inventors: Tao Wang, Farmington, CT (US); Zhongxing Zhang, Madison, CT (US); Eric P. Gillis, Cheshire, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/433,841

(22) PCT Filed: Oct. 15, 2013

(86) PCT No.: PCT/US2013/064977
§ 371 (c)(1),
(2) Date: Apr. 6, 2015

(87) PCT Pub. No.: WO2014/062636
PCT Pub. Date: Apr. 24, 2014

(65) Prior Publication Data
US 2015/0274753 A1    Oct. 1, 2015

Related U.S. Application Data

(60) Provisional application No. 61/715,734, filed on Oct. 18, 2012.

(51) Int. Cl.
| A61K 31/53 | (2006.01) |
| C07D 498/16 | (2006.01) |
| C07D 498/06 | (2006.01) |
| C07D 498/08 | (2006.01) |
| C07D 498/22 | (2006.01) |

(52) U.S. Cl.
CPC ............ *C07D 498/06* (2013.01); *C07D 498/08* (2013.01); *C07D 498/16* (2013.01); *C07D 498/22* (2013.01)

(58) Field of Classification Search
CPC ............................... A61K 31/53; C07D 498/16
USPC ........................................... 540/456; 514/245
See application file for complete search history.

(56) References Cited

U.S. PATENT DOCUMENTS

| 4,816,064 | A | 3/1989 | Konno et al. |
| 7,163,943 | B2 | 1/2007 | Timmer et al. |
| 7,169,785 | B2 | 1/2007 | Timmer et al. |
| 8,445,490 | B2 | 5/2013 | Wang et al. |
| 8,586,584 | B2 | 11/2013 | Wang et al. |
| 8,629,150 | B2 | 1/2014 | Wang et al. |
| 8,697,706 | B2 | 4/2014 | Sun et al. |
| 8,741,884 | B2 | 6/2014 | Wang et al. |
| 8,765,944 | B2 | 7/2014 | Sun et al. |
| 8,871,753 | B2 | 10/2014 | Combs et al. |
| 8,916,702 | B2 * | 12/2014 | Wang .................. C07D 513/04 544/212 |
| 8,933,066 | B2 | 1/2015 | Wang et al. |

FOREIGN PATENT DOCUMENTS

| KR | 2004-0033100 A | 4/2004 |
| WO | WO 02/079187 A1 | 10/2002 |
| WO | WO 2004/026881 A1 | 4/2004 |
| WO | WO 2004/089286 A2 | 10/2004 |
| WO | WO 2008/057209 A1 | 5/2008 |
| WO | WO 2009/091388 A2 | 7/2009 |
| WO | WO 2009/132202 A2 | 10/2009 |
| WO | WO 2010/036896 A1 | 4/2010 |
| WO | WO 2010/118367 A2 | 10/2010 |

* cited by examiner

*Primary Examiner* — Golam M M Shameem
(74) *Attorney, Agent, or Firm* — James Epperson

(57) ABSTRACT

The disclosure provides compounds of formula I, including pharmaceutically acceptable salts, as well as compositions and methods of using the compounds. The compounds have activity against hepatitis C virus (HCV) and may be useful in treating those infected with HCV.

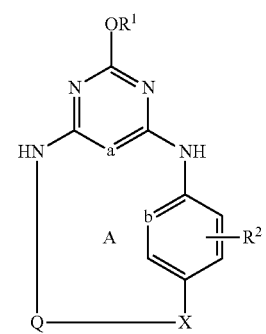

15 Claims, No Drawings

COMPOUNDS FOR THE TREATMENT OF HEPATITIS C

BACKGROUND OF THE INVENTION

The disclosure generally relates to the novel compounds of formula I including pharmaceutically acceptable salts, which have activity against hepatitis C virus (HCV) and are useful in treating those infected with HCV. The disclosure also relates to compositions and methods of using these compounds.

Hepatitis C virus (HCV) chronically infects an estimated 170 million people worldwide, with 3 to 4 million infected individuals in the United States alone (Boyer, N. and Marcellin, P. *J. Hepatology.* 2000, 32:98-112; Alter, M. J., et al. *Engl. J. Med.* 1999, 341:556-562). Prior to the mid 1990s, transfusion with infected blood products was the main route of HCV transmission. Following the introduction of blood screening methods, transmission via injection drug use became the primary risk factor. Chronic infection often leads to the development of severe liver complications, including fibrosis, cirrhosis, and hepatocellular carcinoma. HCV infection is also the leading cause of orthotopic liver transplantation in the United States. The degree to which disease progression is related to viral and cellular factors is not completely understood.

Considerable heterogeneity is found within the nucleotide and encoded amino acid sequence of the HCV genome (Simmonds, P. *J. Gen. Virology.* 2004, 85:3173-3188). Based on this sequence diversity, six major genotypes and multiple associated subtypes have been described. The genotypes of HCV differ in their worldwide distribution, and the clinical significance of the genetic heterogeneity of HCV remains elusive despite numerous studies of the possible effect of genotypes on pathogenesis and therapy.

Medical treatment for HCV is limited by the lack of a vaccine or approved therapies that specifically target the virus. Currently, patients undergo treatment with a combination of parenterally administered pegylated alpha-interferon and oral ribavirin. Genotype 1 HCV is the most difficult to treat and elimination of the virus (sustained virologic response) is achieved for only approximately 50% of patients (Fried, M. W. et al. *N. Engl. J. Med.* 2002, 347:975-982; Zeumzem, S. *Nature Clinical Practice.* 2008, 5:610-622). This poor treatment response, combined with often severe side effects induced by therapy, highlight a need for improved antiviral drugs with better efficacy and safety profiles.

HCV is a member of the Flaviviridae family of viruses with a single-stranded positive-sense RNA genome. Following infection of host cells, the 9.6 Kb genome is translated into a polyprotein precursor of approximately 3,000 amino acids (reviewed in Lindenbach, B. D. and Rice, C. M. *Nature.* 2005, 436:933-938; Moradpour, D, Penin, F., and Rice, C. M. *Nature Reviews.* 2007, 5:453-463). Post-translational processing by both cellular and viral proteases results in the generation of at least 10 separate viral proteins. The structural proteins (which by definition are found in mature virions) include core, E1, E2, and possibly p7, and originate from the amino-terminal region of the polyprotein. The core protein assembles into the viral nucleocapsid. The E1 and E2 glycoproteins form heterodimers that are found within the lipid envelope surrounding the viral particles, and mediate host cell receptor binding and entry of the virus into cells. It is unclear if p7 is a structural protein, and its role in replication has yet to be defined. However p7 is believed to form an ion channel in cellular membranes, preventing acidification of intracellular compartments in which virions are assembled, and it has been shown to be essential for viral replication and assembly. The nonstructural proteins NS2, NS3, NS4A, NS4B, NS5A, and NS5B are produced through maturational cleavages of the carboxy-terminal region of the polyprotein. NS2 along with the amino terminus of NS3 form the NS2-3 metalloprotease which cleaves at the NS2-NS3 junction. Additionally, NS2 is involved in assembly and egress of nascent virions. The NS3 protein contains both a serine protease in its amino-terminal region, and a nucleotide-dependent RNA helicase in its carboxy-terminal region. NS3 forms a heterodimer with the NS4A protein, constituting the active protease which mediates cleavages of the polyprotein downstream of NS3, both in cis, at the NS3-NS4A cleavage site, and in trans, for the remaining NS4A-NS4B, NS4B-NS5A, NS5A-NS5B sites. The complex formation of the NS3 protein with NS4A seems necessary to the processing events, enhancing the proteolytic efficiency at all of the sites. The NS3 protein also exhibits nucleoside triphosphatase and RNA helicase activities. The NS4B protein has been shown to be important for localization of HCV proteins into replication complexes in altered membranous structures within the cell. NS5B encodes an RNA-dependent RNA polymerase that is involved in the replication of HCV.

Subgenomic HCV replicons, containing the untranslated regions 5' and 3' to the coding sequence fused to the nonstructural proteins or the full-length polyprotein, are competent for translation, viral protein expression, and replication within cultured cells (Lohmann, V. et al. *Science.* 1999, 285:110-113; Moradpour, D, Penin, F., and Rice, C. M. *Nature Reviews.* 2007, 5:453-463). The replicon system has proven valuable for the identification of inhibitors targeting the nonstructural proteins associated with these functions. However, only limited subsets of HCV genotypes have been used to generate functional replicons.

Other systems have been used to study the biology of the HCV structural proteins that mediate the entry into host cells. For example, virus-like-particles made in recombinant baculovirus-infected cells with the HCV core, E1 and E2 proteins have also been used to study the function of the HCV E1 and E2 proteins (Barth, H., et al. *J. Biol. Chem.* 2003, 278:41003-41012). In addition, pseudotyping systems where the E1 and E2 glycoproteins are used to functionally replace the glycoproteins of retroviruses have been developed (Bartosch, B., Dubuisson, J. and Cosset, F.-L. *J. Exp. Med.* 2003, 197:633-642; Hsu, M. et al. *Proc. Natl. Acad. Sci. USA.* 2003, 100: 7271-7276). These systems yield HCV pseudoparticles that bind to and enter host cells in a manner which is believed to be analogous to the natural virus, thus making them a convenient tool to study the viral entry steps as well as to identify inhibitors block this process.

Recently, a full-length genotype 2a HCV clone, JFH1, was isolated and demonstrated the ability to replicate in vitro. Through repeated passage and adaptation in cell culture increased titers of infectious virus were produced (Lindenbach, B. D., et al. *Science.* 2005, 309:623-626; Wakita, T. et al. *Nature Med.* 2005, 11:791-796). In contrast to the HCV replicon or pseudotyping systems, the infectious virus is useful for studying the complete HCV replication cycle, including identifying inhibitors of not only the replication proteins, but those involved in early steps in virus infection (entry and uncoating) and production of progeny viruses (genome packaging, nucleocapsid assembly, virion envelopment and egress).

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I

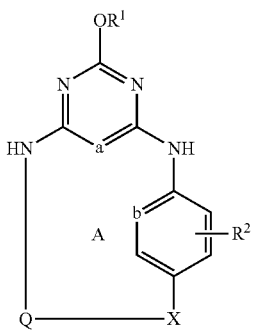

a is C or N;
b is C or N;
R¹ is alkyl, hydroxyalkyl, alkoxyalkyl, haloalkyl, cycloalkyl, hydroxycycloalkyl, alkoxycycloalkyl, halocycloalkyl, cycloalkenyl, benzyl, indanyl, or alkylcarbonyl;
R² is hydrogen, cyano, halo, alkyl, haloalkyl, alkoxy, or haloalkoxy;
R³ is hydrogen, alkyl, alkylcarbonyl, alkoxycarbonyl, benzyloxycarbonyl, aminocarbonyl, alkylaminocarbonyl, or dialkyaminocarbonyl;
R⁴ is hydrogen or alkyl;
R⁵ is hydrogen or alkyl;
R⁶ is hydrogen, alkyl, (cycloalkyl)alkyl, (Ar¹)alkyl, cycloalkyl, (alkyl)cycloalkyl, tetralinyl, Ar¹;
R⁷ is hydrogen or alkyl;
or R⁶ and R⁷ taken together with the nitrogen to which they are attached is azetidinyl, pyrrolidinyl, piperidinyl, piperazinyl, or morpholinyl, and is substituted with 0-3 substituents selected from alkyl, alkylcarbonyl, and alkoxycarbonyl;
Q is an alkylene or alkenylene chain containing 0-6 groups selected from the group consisting of O, NR³, S, S(O), S(O₂), C(O)O, C(O)NR⁴, OC(O)NR⁴, NR⁴C(O)NR⁴, and Z, provided that any O or S atom does not directly bond to another O or S atom, such that ring A is 13-32 membered; and where the alkylene or alkenylene chain contains 1 NR⁴COCOOR⁵ or NR⁴COCONR⁶R⁷, and where the alkylene or alkenylene chain contains 0-6 substituents selected from the group consisting of alkyl, hydroxy, alkoxy, and phenyl where the phenyl substituent is further substituted with 0-4 cyano, halo, alkyl, haloalkyl, alkoxy, or haloalkoxy substituents;
Ar¹ is phenyl, pyridinyl, pyrazolyl, isoxazolyl, isothiazolyl, imidazolyl, oxazolyl, thiazolyl, triazolyl, oxadiazolyl, or thiadiazolyl, and is substituted with 0-3 substituents selected from cyano, halo, alkyl, haloalkyl, hydroxy, alkoxy, or haloalkoxy;
X is O, CH₂, CO, CO₂, or C(O)NR⁴; and
Z is C₃₋₇ cycloalkylene, phenylene, pyrrolidindiyl, piperidindiyl, or piperazindiyl;
or a pharmaceutically acceptable salt thereof.

Another aspect of the invention is a compound of formula I where
a is C or N;
b is C or N;
R¹ is haloalkyl;
R² is hydrogen;
R⁴ is hydrogen or alkyl;
R⁵ is hydrogen or alkyl;
R⁶ is hydrogen, alkyl, (cycloalkyl)alkyl, (Ar¹)alkyl, cycloalkyl, (alkyl)cycloalkyl, tetralinyl, Ar¹;
R⁷ is hydrogen or alkyl;
or R⁶ and R⁷ taken together with the nitrogen to which they are attached is azetidinyl, pyrrolidinyl, piperidinyl, piperazinyl, or morpholinyl, and is substituted with 0-3 substituents selected from alkyl, alkylcarbonyl, and alkoxycarbonyl;
Q is an alkylene or alkenylene chain containing 2 groups selected from the group consisting of O and Z, provided that any O does not directly bond to another O atom, such that ring A is 13-32 membered; and where the alkylene or alkenylene chain contains 1 NR⁴COCOOR⁵ or NR⁴COCONR⁶R⁷;
Ar¹ is phenyl, isoxazolyl, thiazolyl, or thiadiazolyl, and is substituted with 0-3 substituents selected from cyano, halo, alkyl, haloalkyl, hydroxy, alkoxy, or haloalkoxy;
X is C(O)NR⁴; and
Z is phenylene;
or a pharmaceutically acceptable salt thereof.

Another aspect of the invention is a compound of formula I where a is N.
Another aspect of the invention is a compound of formula I where a is C.
Another aspect of the invention is a compound of formula I where b is C.
Another aspect of the invention is a compound of formula I where b is N.
Another aspect of the invention is a compound of formula I where Q is an alkylene or alkenylene chain containing 2 groups selected from the group consisting of O and Z, provided that any O does not directly bond to another O atom, such that ring A is 13-32 membered; and where the alkylene or alkenylene chain contains 1 NR⁴COCOOR⁵ or NR⁴COCONR⁶R⁷;
Another aspect of the invention is a compound of formula I where Q is an alkylene or alkenylene chain containing 1 O and 1 Z, such that ring A is 13-32 membered; and where the alkylene or alkenylene chain contains 1 NR⁴COCOOR⁵ or NR⁴COCONR⁶R⁷.

Another aspect of the invention is a compound of formula I where R⁴ is hydrogen or alkyl, R⁵ is hydrogen or alkyl, R⁶ is hydrogen, alkyl, (cycloalkyl)alkyl, (Ar¹)alkyl, cycloalkyl, (alkyl)cycloalkyl, tetralinyl, or Ar¹; R⁷ is hydrogen or alkyl; or R⁶ and R⁷ taken together with the nitrogen to which they are attached is azetidinyl, pyrrolidinyl, piperidinyl, piperazinyl, or morpholinyl, and is substituted with 0-3 substituents selected from alkyl, alkylcarbonyl, and alkoxycarbonyl.

Another aspect of the invention is a compound of formula I where Ar¹ is phenyl, isoxazolyl, thiazolyl, or thiadiazolyl, and is substituted with 0-3 substituents selected from cyano, halo, alkyl, haloalkyl, hydroxy, alkoxy, or haloalkoxy;
Another aspect of the invention is a compound of formula I where X is C(O)NR⁴.
Another aspect of the invention is a compound of formula I where Z is phenylene.
Any scope of any variable, including a, b, R¹, R², R³, R⁴, R⁵, R⁶, R⁷, Q, X and Z, can be used independently with the scope of any other instance of a variable.

Unless specified otherwise, these terms have the following meanings "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Alkylene" means a straight or branched divalent alkyl group composed of 1 to 6 carbons. "Alkenylene" means a straight or branched divalent alkyl group composed of 2 to 6 carbons with at least one double bond. For ring A, Q is an alkylene or alkenylene chain with sufficient carbons and optionally other defined groups to form a 13-32 membered ring. "Cycloalkylene" means a divalent cycloalkane moiety composed of 3 to 7 carbons and includes gem-divalency (for example 1,1-cyclopropanediyl) as well as non-gem-divalency (for example, 1,4-cyclohexanediyl). Phenylene is a divalent benzene ring. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The substituents described above may be attached at any suitable point of attachment unless otherwise specified. However, it is understood that the compounds encompassed by the present invention are those that are chemically stable as understood by those skilled in the art. Additionally, the compounds encompassed by the present disclosure are those that are suitably stable for use as a pharmaceutical agent.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the structures below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

BIOLOGICAL METHODS

Infection Assays.

HCV pseudoparticles, produced using standardized methodology (Bartosch, B., Dubuisson, J. and Cosset, F.-L. J. *Exp. Med.* 2003, 197:633-642) were made via a liposome-based transfection procedure of 293T cells with plasmids expressing the murine leukemia virus capsid and polymerase proteins, an MLV genome encoding the luciferase reporter gene, and envelope glycoproteins from either HCV or vesicular stomatitis virus (VSV). The genotype 1a HCV E1 and E2 envelope coding sequences were derived from the H77C isolate (GenBank accession number AF009606). Media containing pseudoparticles was collected 3 days following transfection, filtered, and stored at −20° C. as a viral stock. Infections were performed in 384-well plates by mixing pseudovirus with $1\times10^4$ Huh7 cells/well in the presence or absence of test inhibitors, followed by incubation at 37° C. Luciferase activity, reflecting the degree of entry of the pseudoparticles into host cells, was measured 2 days after infection. The specificity of the compounds for inhibiting HCV was determined by evaluating inhibition of VSV pseudoparticle infection.

Compounds and Data Analysis.

Test compounds were serially diluted 3-fold in dimethyl sulfoxide (DMSO) to give a final concentration range in the assay of 50.0 μM to 0.04 pM. Maximum activity (100% of control) and background were derived from control wells containing DMSO but no inhibitor or from uninfected wells, respectively. The individual signals in each of the compound test wells were then divided by the averaged control values after background subtraction and multiplied by 100% to determine percent activity. Assays were performed in duplicate and average $EC_{50}$ values (reflecting the concentration at which 50% inhibition of virus replication was achieved) were calculated. Compound $EC_{50}$ data is expressed as A:=0.1-100 nM; B=100-1000 nM; C=1000-5000 nM). Representative data for compounds are reported in Table 1.

TABLE 1

| Example | Structure | $EC_{50}$ (nM) 1a (H77C) | $EC_{50}$ (nM) 1a (H77C) |
|---------|-----------|--------------------------|--------------------------|
| 1001 | 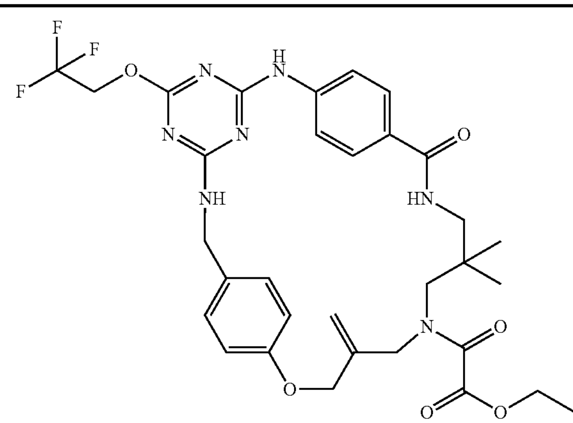 | A | 0.6292 |

TABLE 1-continued
| Example | Structure | EC$_{50}$ (nM) 1a (H77C) | EC$_{50}$ (nM) 1a (H77C) |
|---|---|---|---|
| 1002 | 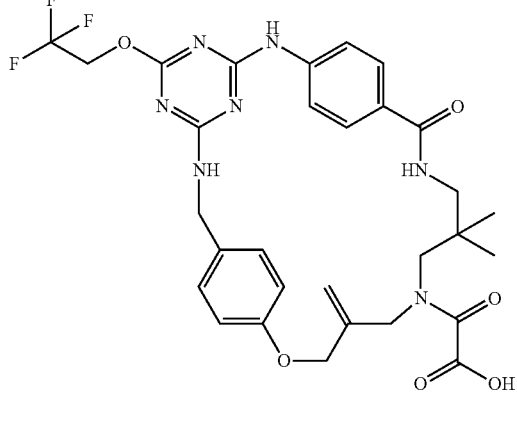 | A | 5.734 |
| 1003 | 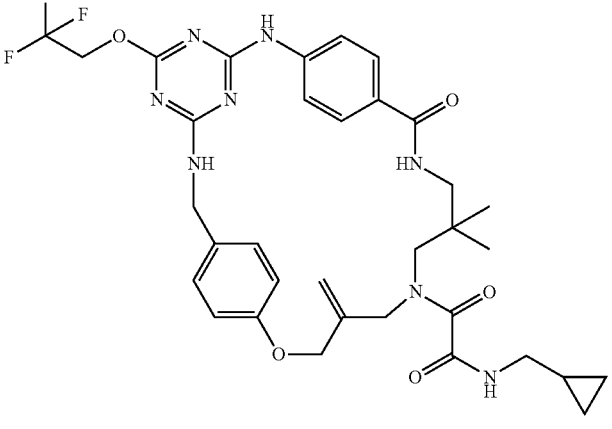 | A | |
| 1004 | 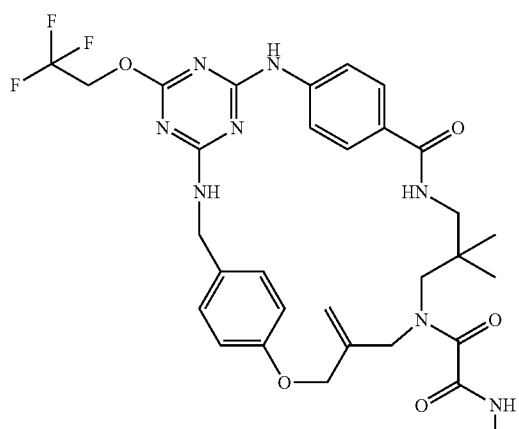 | A | |

TABLE 1-continued

| Example | Structure | EC$_{50}$ (nM) 1a (H77C) | EC$_{50}$ (nM) 1a (H77C) |
|---|---|---|---|
| 2003 | 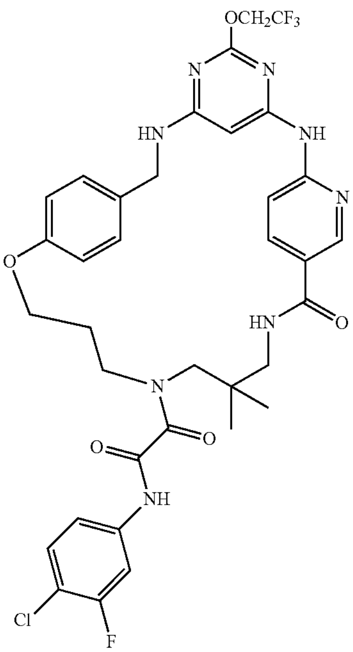 | A | 0.1055 |
| 2004 | 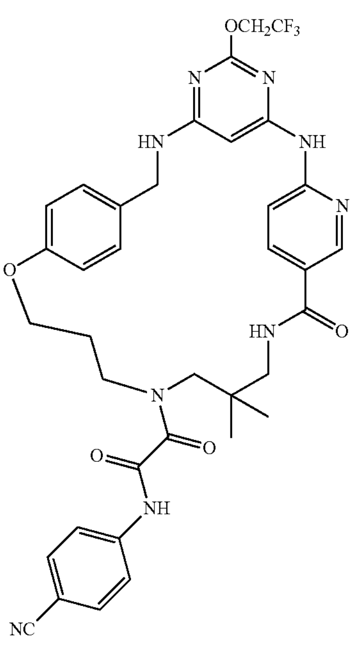 | A | |

TABLE 1-continued
| Example | Structure | EC$_{50}$ (nM) 1a (H77C) | EC$_{50}$ (nM) 1a (H77C) |
|---|---|---|---|
| 3001 | 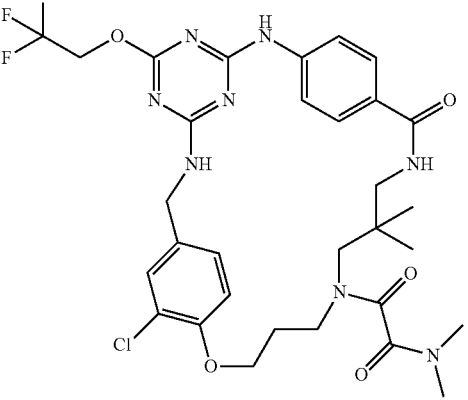 | A | |
| 3002 | 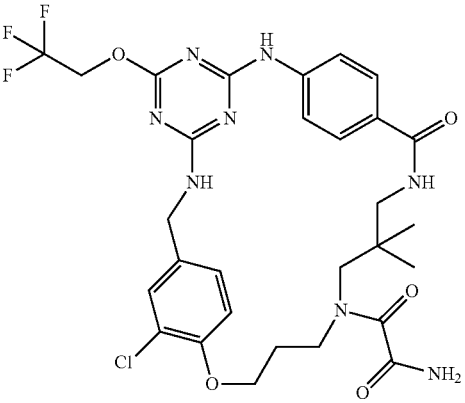 [SMILES: CC1(C)CNC(=O)c2ccc(cc2)Nc2nc(nc(OCC(F)(F)F)n2)NCc2ccc(c(Cl)c2)OCCCN(C(=O)C(N)=O)C1] | A | |
| 3003 | 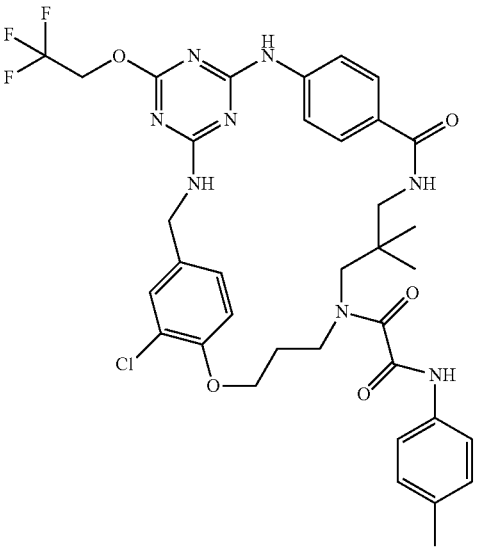 [SMILES: Cc1ccc(NC(=O)C(=O)N2CCCOc3ccc(cc3Cl)CNc3nc(nc(OCC(F)(F)F)n3)Nc3ccc(cc3)C(=O)NCC(C)(C)C2)cc1] | A | |

TABLE 1-continued
| Example | Structure | EC$_{50}$ (nM) 1a (H77C) | EC$_{50}$ (nM) 1a (H77C) |
|---|---|---|---|
| 3004 | 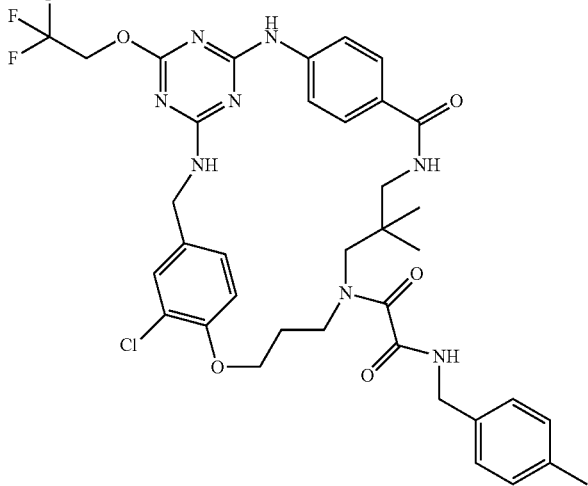 | A | |
| 3005 | 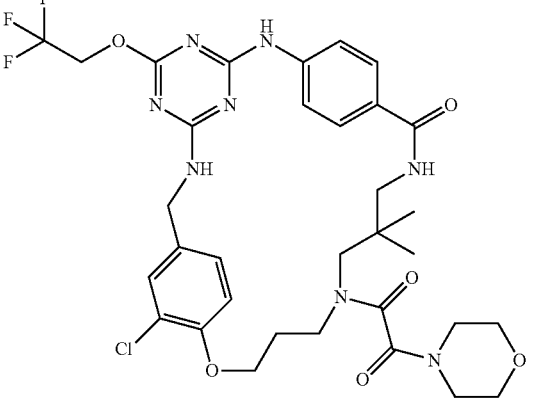 | A | |
| 3006 | 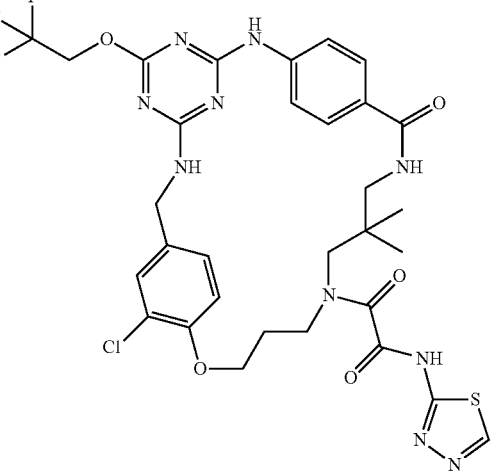 | A | |

TABLE 1-continued
| Example | Structure | EC$_{50}$ (nM) 1a (H77C) | EC$_{50}$ (nM) 1a (H77C) |
|---|---|---|---|
| 3007 | 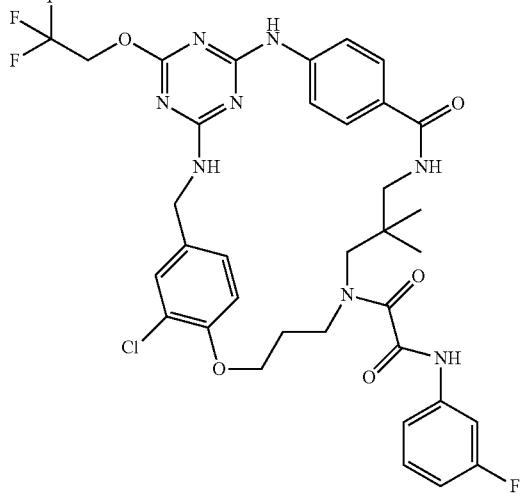 | A | |
| 3008 | 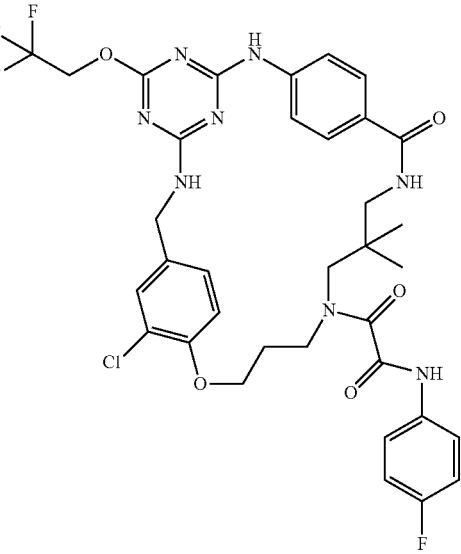 | A | 2.42 |
| 3009 | 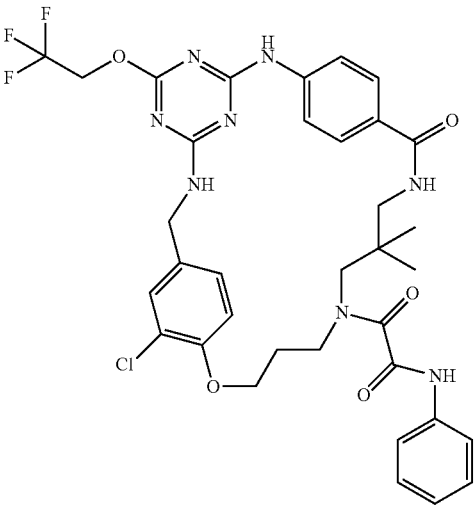 [SMILES: CC1(C)CNC(=O)c2ccc(cc2)Nc2nc(nc(OCC(F)(F)F)n2)NCc2ccc(c(Cl)c2)OCCCN(C(=O)C(=O)Nc2ccccc2)C1] | A | |

TABLE 1-continued

| Example | Structure | EC$_{50}$ (nM) 1a (H77C) | EC$_{50}$ (nM) 1a (H77C) |
|---------|-----------|--------------------------|--------------------------|
| 3010 | 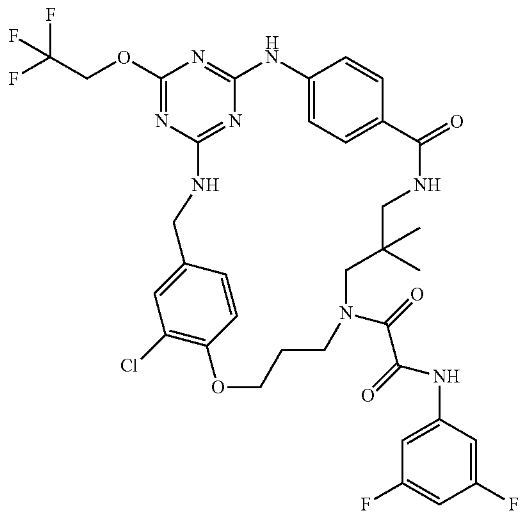 [SMILES: CC1(C)CNC(=O)c2ccc(cc2)Nc2nc(nc(OCC(F)(F)F)n2)NCc2ccc(c(Cl)c2)OCCCN(C(=O)C(=O)Nc2cc(F)cc(F)c2)C1] | A | |
| 3011 | 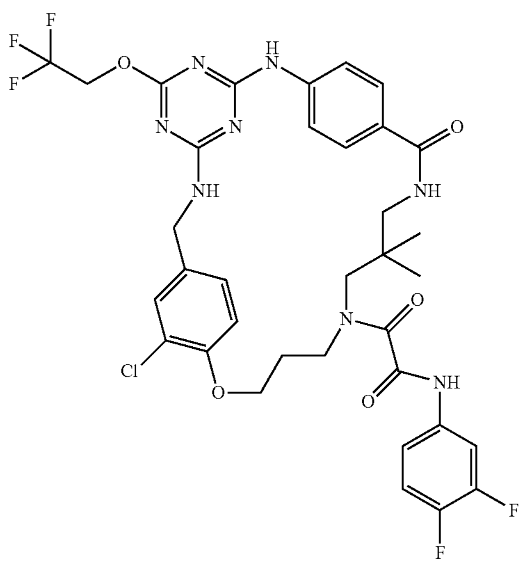 [SMILES: CC1(C)CNC(=O)c2ccc(cc2)Nc2nc(nc(OCC(F)(F)F)n2)NCc2ccc(c(Cl)c2)OCCCN(C(=O)C(=O)Nc2ccc(F)c(F)c2)C1] | A | |
| 3012 | 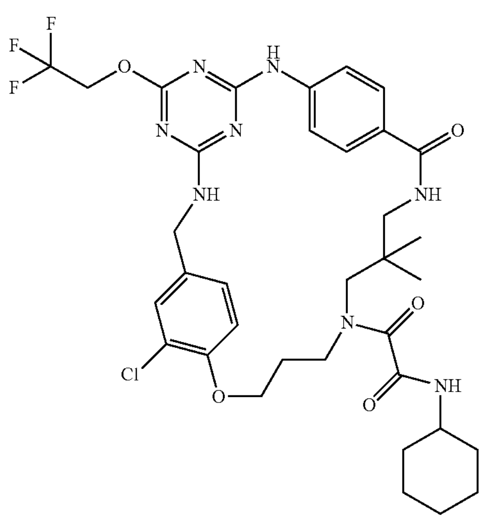 [SMILES: CC1(C)CNC(=O)c2ccc(cc2)Nc2nc(nc(OCC(F)(F)F)n2)NCc2ccc(c(Cl)c2)OCCCN(C(=O)C(=O)NC2CCCCC2)C1] | A | |

TABLE 1-continued
| Example | Structure | EC$_{50}$ (nM) 1a (H77C) | EC$_{50}$ (nM) 1a (H77C) |
|---|---|---|---|
| 3013 | 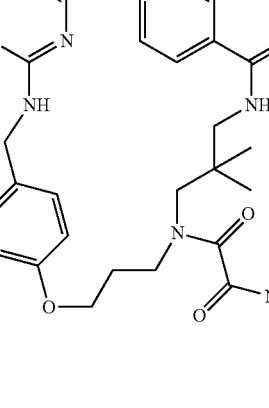 | A | |
| 3014 | 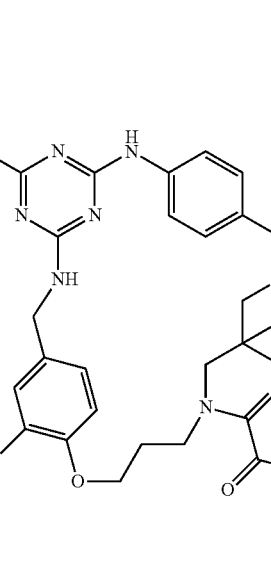 | A | |
| 3015 | 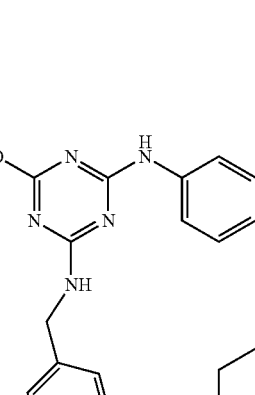 | A | |

TABLE 1-continued
| Example | Structure | EC$_{50}$ (nM) 1a (H77C) | EC$_{50}$ (nM) 1a (H77C) |
|---|---|---|---|
| 3016 | 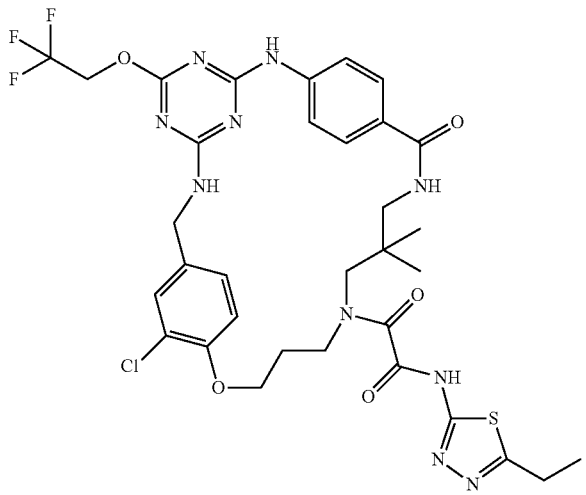 [SMILES: CCc1nnc(NC(=O)C(=O)N2CCCOc3ccc(cc3Cl)CNc3nc(nc(OCC(F)(F)F)n3)Nc3ccc(cc3)C(=O)NCC(C)(C)C2)s1] | A | 24.03 |
| 3017 | 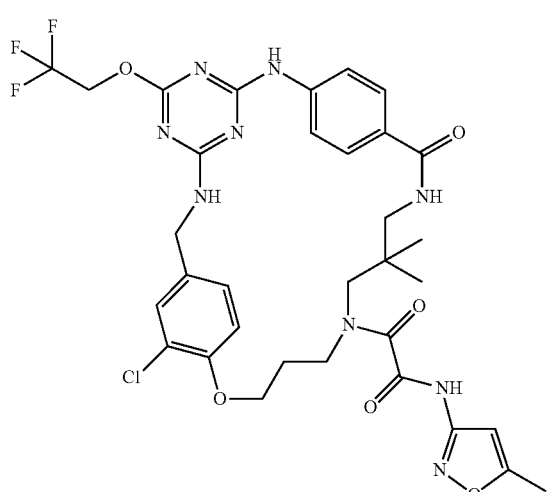 | A | |
| 3018 | 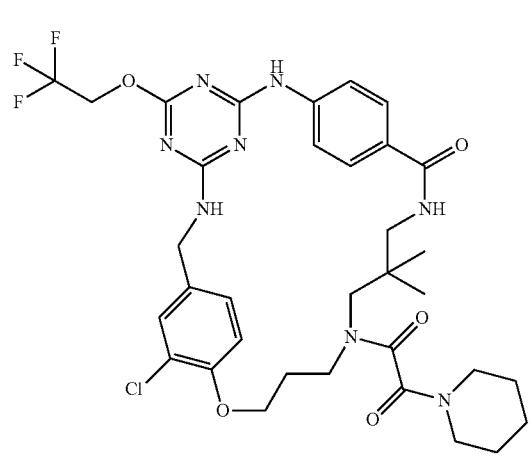 [SMILES: CC1(C)CNC(=O)c2ccc(cc2)Nc2nc(nc(OCC(F)(F)F)n2)NCc2ccc(c(Cl)c2)OCCCN(C(=O)C(=O)N2CCCCC2)C1] | A | |

TABLE 1-continued

| Example | Structure | EC$_{50}$ (nM) 1a (H77C) | EC$_{50}$ (nM) 1a (H77C) |
|---|---|---|---|
| 3019 | 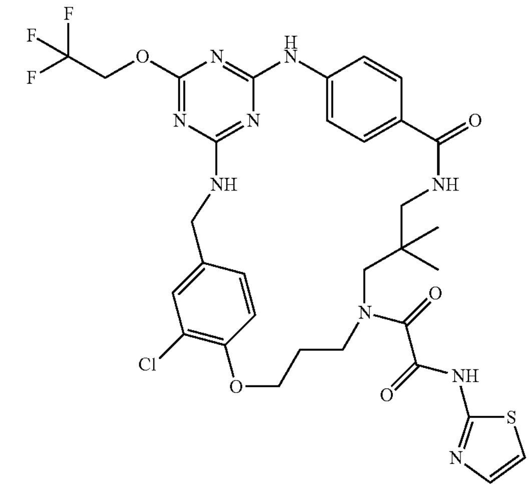 [SMILES: CC1(C)CNC(=O)c2ccc(cc2)Nc2nc(nc(OCC(F)(F)F)n2)NCc2ccc(c(Cl)c2)OCCCN(C(=O)C(=O)Nc2nccs2)C1] | A | |
| 3020 | 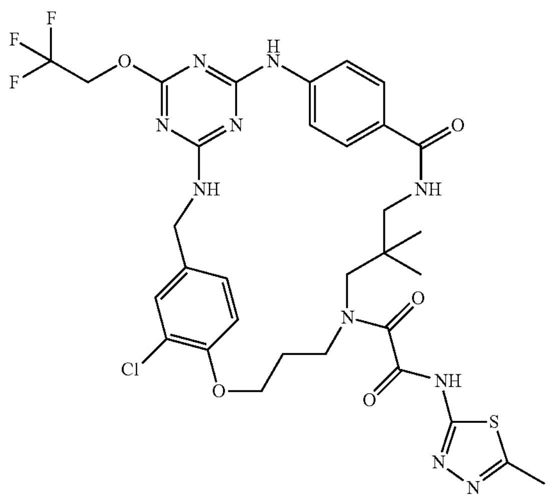 [SMILES: Cc1nnc(NC(=O)C(=O)N2CCCOc3ccc(cc3Cl)CNc3nc(nc(OCC(F)(F)F)n3)Nc3ccc(cc3)C(=O)NCC(C)(C)C2)s1] | A | |

PHARMACEUTICAL COMPOSITIONS AND METHODS OF TREATMENT

The compounds demonstrate activity against HCV and can be useful in treating HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
|---|---|---|
| Omega IFN | IFN-ω | Intarcia Therapeutics |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon - α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |

TABLE 2-continued

| Brand Name | Type of Inhibitor or Target | Source Company |
|---|---|---|
| Pegasys and Ceplene | PEGylated IFN-α2a/ immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmaceuticals Inc., Bethesda, MD/ SciClone Pharmaceuticals Inc, San Mateo, CA |
| Levovirin | IMPDH inhibitor | Ribapharm Inc., Costa Mesa, CA |
| Viramidine | Ribavirin Prodrug | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ ribavirin | Schering-Plough Corporation, Kenilworth, NJ |
| Ribavirin | ribavirin | Schering-Plough Corporation, Kenilworth, NJ |
| PEG-Intron/ Ribavirin | PEGylated IFN-α2b/ribavirin | Schering-Plough Corporation, Kenilworth, NJ |
| Zadazim | Immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| Batabulin (T67) | β-tubulin inhibitor | Tularik Inc., South San Francisco, CA |
| Merimepodib (VX-497) | IMPDH inhibitor | Vertex Pharmaceuticals Inc., Cambridge, MA |
| Telaprevir (VX-950, LY-570310) | NS3 serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-6865 (XTL-002) | monoclonal antibody | XTL Biopharmaceuticals Ltd., Rehovot, Isreal |
| HCV-796 | NS5B Replicase Inhibitor | Wyeth/Viropharma |
| NM-283 | NS5B Replicase Inhibitor | Idenix/Novartis |
| GL-59728 | NS5B Replicase Inhibitor | Gene Labs/Novartis |
| GL-60667 | NS5B Replicase Inhibitor | Gene Labs/Novartis |
| 2'C MeA | NS5B Replicase Inhibitor | Gilead |
| PSI 6130 | NS5B Replicase Inhibitor | Roche |
| R1626 | NS5B Replicase Inhibitor | Roche |
| SCH 503034 | serine protease inhibitor | Schering Plough |
| NIM811 | Cyclophilin Inhibitor | Novartis |
| Suvus | Methylene blue | Bioenvision |
| Multiferon | Long lasting IFN | Viragen/Valentis |
| Actilon (CPG10101) | TLR9 agonist | Coley |
| Interferon-β | Interferon-β-1a | Serono |
| Zadaxin | Immunomodulator | Sciclone |
| Pyrazolopyrimidine compounds and salts From WO-2005047288 26 May 2005 | HCV Inhibitors | Arrow Therapeutics Ltd. |
| 2'C Methyl adenosine | NS5B Replicase Inhibitor | Merck |
| GS-9132 (ACH-806) | HCV Inhibitor | Achillion/Gilead |

SYNTHETIC METHODS

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

For the section of compounds in the 0000 series all Liquid Chromatography (LC) data were recorded on a Shimadzu LC-10AS or LC-20AS liquid chromotograph using a SPD-10AV or SPD-20A UV-Vis detector and Mass Spectrometry (MS) data were determined with a Micromass Platform for LC in electrospray mode.

HPLC Method (i.e., Compound Isolation).

Compounds purified by preparative HPLC were diluted in methanol (1.2 mL) and purified using a Shimadzu LC-8A or LC-10A automated preparative HPLC system.

EXAMPLES

Preparation of Compound 1001

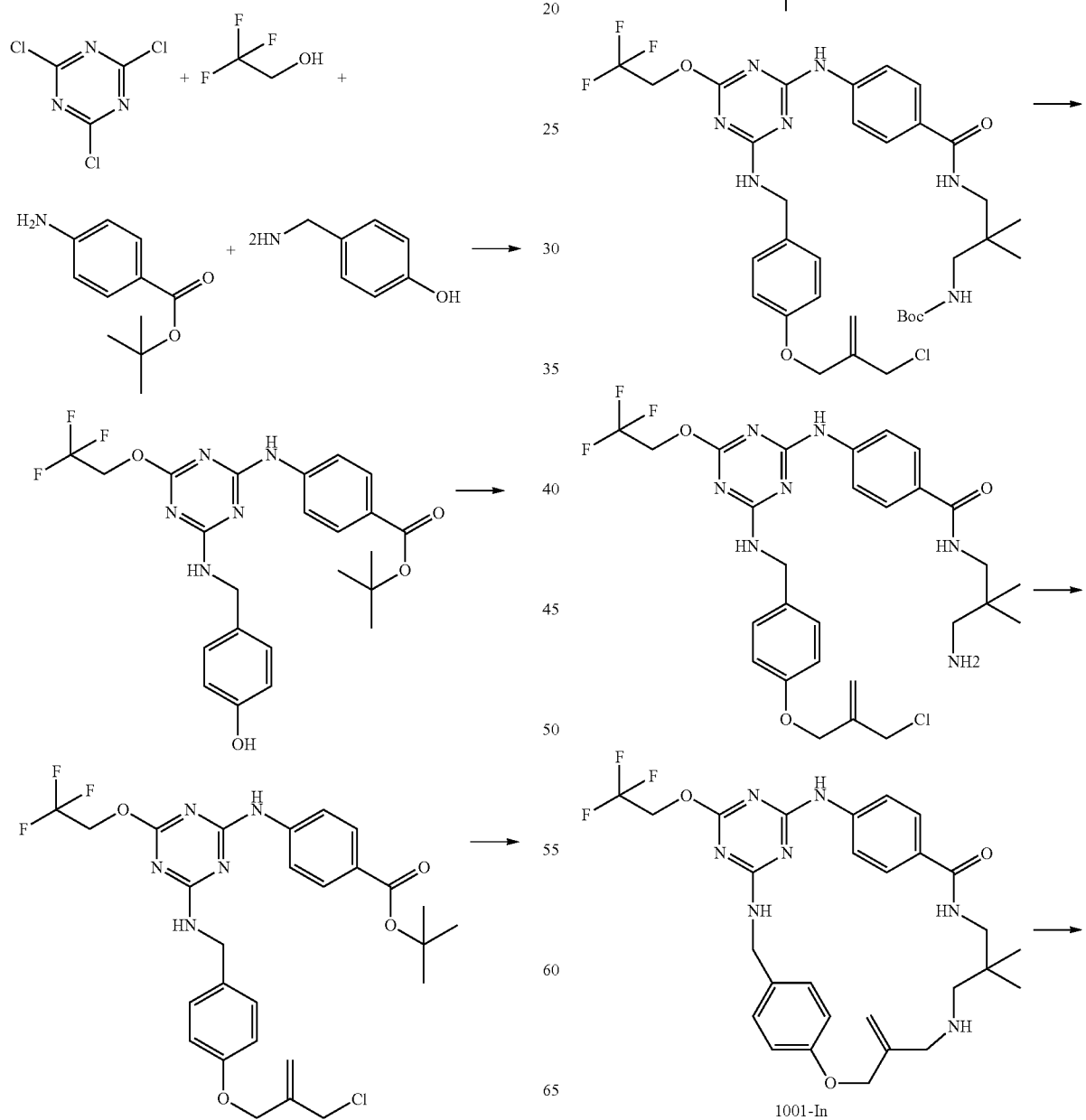

-continued

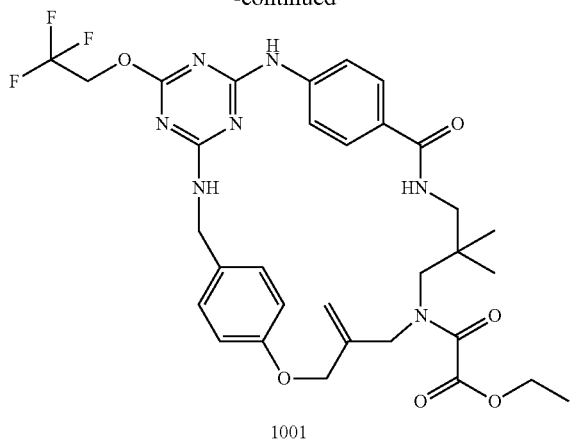

1001

Step 1: To a solution of 2,4,6-trichloro-1,3,5-triazine (8 g) in acetone (250 mL) was added a solution of 2,2,2-trifluoroethanol (4.77 g) and 2,4,6-Collidine (6.31 mL) in acetone (100 mL) dropwise over 20 minutes. The resulting mixture was stirred at room temperature for 16 hours. All the solvents were removed under vacuum to give a residue which was diluted with NMP (100 mL), followed by addition of tert-butyl 4-aminobenzoate (9.22 g) and DIPEA (22.73 mL). After stirring at room temperature for 16 hours, 4-(aminomethyl)phenol (5.88 g) was added. The resulting mixture was stirred for 2 days at room temperature. Then, the mixture was diluted with 300 mL of water and extracted with EtOAc (2×300 mL). The organic layers were combined, washed with brine (2×150 mL), dried over MgSO₄ and concentrated. The residue was purified by silica gel column (hexane:EtOAc=3:2) to give tert-butyl 4-(4-(4-hydroxybenzylamino)-6-(2,2,2-trifluoroethoxy)-1,3,5-triazin-2-ylamino)benzoate (12 g).

| tert-butyl 4-(4-(4-hydroxybenzylamino)-6-(2,2,2-trifluoroethoxy)-1,3,5-triazin-2-ylamino)benzoate | |
|---|---|
| MS (M + H)⁺ Calcd. | 492.2 |
| MS (M + H)⁺ Observ. | 492.2 |
| Retention Time | 1.89 min |
| LC Condition | |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Step 2: A suspension of tert-butyl 4-((4-((4-hydroxybenzyl)amino)-6-(2,2,2-trifluoroethoxy)-1,3,5-triazin-2-yl)amino)benzoate (3 g), 3-chloro-2-(chloromethyl)prop-1-ene (1.15 g) and K₂CO₃ (1.69 g) in acetone (20 mL) was heated to reflux for 16 hours. The solvent was removed under vacuum. The residue was purified by silica gel column (hexanes:EtOAc=10:1 to 4:1) to give tert-butyl 4-(4-(4-(2-(chloromethyl)allyloxy)benzylamino)-6-(2,2,2-trifluoroethoxy)-1,3,5-triazin-2-ylamino)benzoate (1.3 g).

| tert-butyl 4-(4-(4-(2-(chloromethyl)allyloxy)benzylamino)-6-(2,2,2-trifluoroethoxy)-1,3,5-triazin-2-ylamino)benzoate | |
|---|---|
| MS (M + H)⁺ Calcd. | 580.2 |
| MS (M + H)⁺ Observ. | 580.2 |
| Retention Time | 2.31 min |
| LC Condition | |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Step 3: To a solution of tert-butyl 4-((4-((4-((2-(chloromethyl)allyl)oxy)benzyl)amino)-6-(2,2,2-trifluoroethoxy)-1,3,5-triazin-2-yl)amino)benzoate (1.3 g) in DCM (8 mL) was added TFA (3 ml). The mixture was stirred at room temperature for 3 hours. All the solvents were removed under vacuum to give 4-(4-(4-(2-(chloromethyl)allyloxy)benzylamino)-6-(2,2,2-trifluoroethoxy)-1,3,5-triazin-2-ylamino)benzoic acid (1.1 g).

| 4-(4-(4-(2-(chloromethyl)allyloxy)benzylamino)-6-(2,2,2-trifluoroethoxy)-1,3,5-triazin-2-ylamino)benzoic acid | |
|---|---|
| MS (M + H)⁺ Calcd. | 524.1 |
| MS (M + H)⁺ Observ. | 524.0 |
| Retention Time | 2.20 min |
| LC Condition | |
| Solvent A | 90% Water -10% Methanol-0.1% TFA |
| Solvent B | 10% Water -90% Methanol-0.1% TFA |
| Start % B | 30 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Step 4: To a solution of 4-((4-((4-((2-(chloromethyl)allyl)oxy)benzyl)amino)-6-(2,2,2-trifluoroethoxy)-1,3,5-triazin-2-yl)amino)benzoic acid (1.1 g) and TBTU (0.74 g) in NMP (10 mL) was added tert-butyl(3-amino-2,2-dimethylpropyl)carbamate (0.51 g) and DIPEA (1.47 mL). After stirring at room temperature for 2 hours, the mixture was diluted with 100 mL of water and extracted with EtOAc (2×150 mL). The organic layer were combined, washed with brine (100 mL), dried over MgSO₄ and concentrated. The residue was purified by silica gel column to give tert-butyl 3-(4-(4-(4-(2-(chloromethyl)allyloxy)benzylamino)-6-(2,2,2-trifluoroethoxy)-1,3,5-triazin-2-ylamino)benzamido)-2,2-dimethylpropylcarbamate (1 g).

| tert-butyl 3-(4-(4-(4-(2-(chloromethyl)allyloxy)benzylamino)-6-(2,2,2-trifluoroethoxy)-1,3,5-triazin-2-ylamino)benzamido)-2,2-dimethylpropylcarbamate | |
|---|---|
| MS (M + H)⁺ Calcd. | 708.3 |
| MS (M + H)⁺ Observ. | 708.3 |
| Retention Time | 2.19 min |
| LC Condition | |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |

-continued

| | |
|---|---|
| Solvent Pair | Water - Methanol- TFA |
| Column | PHENOMENEX-LUNA 2.0 × 30 mm 3 um |

Step 5: To a solution of tert-butyl(3-(4-((4-((4-((2-(chloromethyl)allyl)oxy)benzyl)amino)-6-(2,2,2-trifluoroethoxy)-1,3,5-triazin-2-yl)amino)benzamido)-2,2-dimethylpropyl)carbamate (1 g) in DCM (10 mL) was added TFA (3 mL). The mixture was stirred at room temperature for 3 hours. All the solvents were removed under vacuum. The residue was diluted with EtOAc (200 mL), washed with 10% of NaHCO₃ (50 mL), brine (50 mL), dried over MgSO₄ and concentrated to give N-(3-amino-2,2-dimethylpropyl)-4-(4-(4-(2-(chloromethyl)allyloxy)benzylamino)-6-(2,2,2-trifluoroethoxy)-1,3,5-triazin-2-ylamino)benzamide (0.8 g).

| N-(3-amino-2,2-dimethylpropyl)-4-(4-(4-(2-(chloromethyl)allyloxy)benzylamino)-6-(2,2,2-trifluoroethoxy)-1,3,5-triazin-2-ylamino)benzamide | |
|---|---|
| MS (M + H)⁺ Calcd. | 608.2 |
| MS (M + H)⁺ Observ. | 608.3 |
| Retention Time | 1.42 min |
| LC Condition | |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Step 6:

A mixture of N-(3-amino-2,2-dimethylpropyl)-4-((4-((4-((2-(chloromethyl)allyl)oxy)benzyl)amino)-6-(2,2,2-trifluoroethoxy)-1,3,5-triazin-2-yl)amino)benzamide (0.8 g) and NaHCO₃ (0.11 g) in acetonitrile (30 mL) was heated at 90° C. in a sealed bottle for 16 hours. The solvent was removed under vacuum. The residue was diluted with EtOAc (250 mL) and washed with water (30 mL), brine (30 mL), dried over MgSO₄ and concentrated. The residue was purified by preparative HPLC to give 1001-In (150 mg).

| 1001-In | |
|---|---|
| MS (M + H)⁺ Calcd. | 572.3 |
| MS (M + H)⁺ Observ. | 572.3 |
| Retention Time | 1.22 min |
| LC Condition | |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Step 7: To a solution of 1001-In (60 mg) in THF (12 mL) was added ethyl 2-chloro-2-oxoacetate (215 mg) and DIPEA (0.37 mL). The mixture was stirred at room temperature for 4 hours. All the solvents were removed under vacuum. The residue was purified by preparative HPLC to give 1001 (30 mg).

| 1001 | |
|---|---|
| MS (M + H)⁺ Calcd. | 672.3 |
| MS (M + H)⁺ Observ. | 672.3 |
| Retention Time | 1.96 min |
| LC Condition | |
| Solvent A | 90% Water -10% Methanol-0.1% TFA |
| Solvent B | 10% Water -90% Methanol-0.1% TFA |
| Start % B | 30 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Preparation of Compound 1002

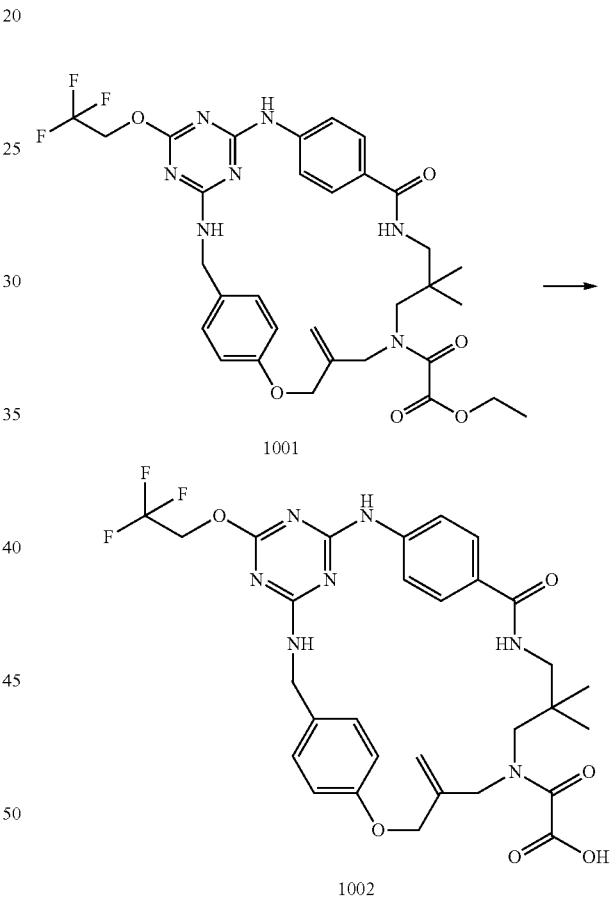

To a solution of 1001 (15 mg) in THF (2 mL) was added K₂CO₃ (61.7 mg) in water (2 mL). The mixture was stirred at room temperature for 16 hours. All the solvents were removed under vacuum. The residue was purified by preparative HPLC to give 1002 (6 mg).

| 1002 | |
|---|---|
| MS (M + H)⁺ Calcd. | 644.2 |
| MS (M + H)⁺ Observ. | 644.4 |
| Retention Time | 1.29 minutes |

| LC Condition | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Preparation of Compound 1003

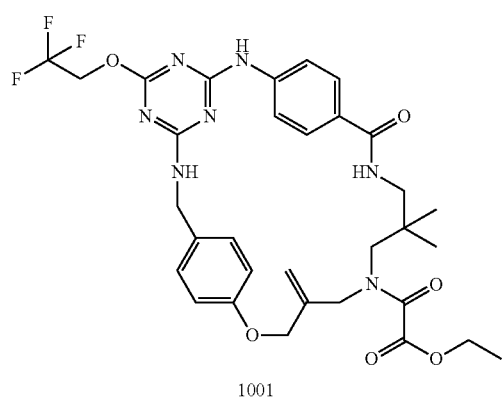

1001

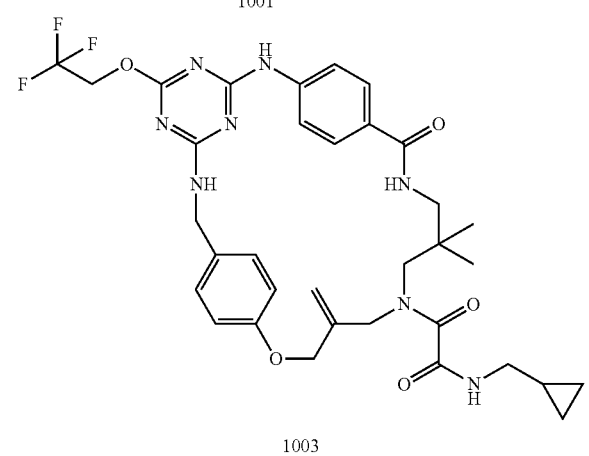

1003

To a solution of 1001 (15 mg) in ethanol (2 mL) was added cyclopropylmethanamine (31.8 mg). After stirring at room temperature for 4 days, the mixture was purified by preparative HPLC to give 1003 (6 mg).

| 1003 | |
|---|---|
| MS (M + H)⁺ Calcd. | 697.3 |
| MS (M + H)⁺ Observ. | 697.4 |
| Retention Time | 1.95 min |
| LC Condition | |
| Solvent A | 90% Water -10% Methanol-0.1% TFA |
| Solvent B | 10% Water -90% Methanol-0.1% TFA |
| Start % B | 30 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Preparation of Compound 1004

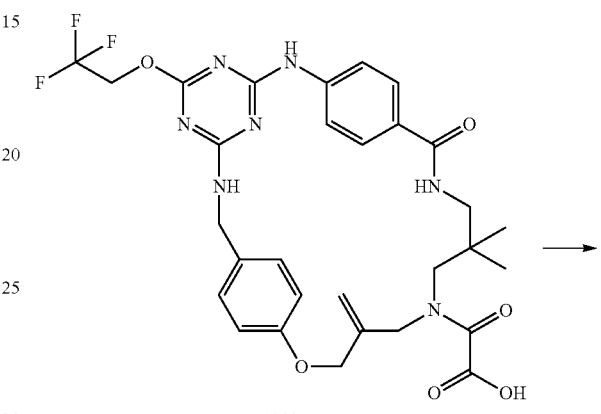

1002

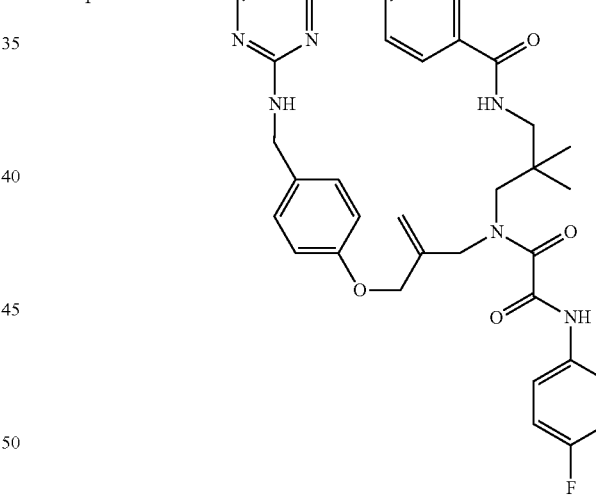

1004

To a solution of 1002 (5 mg) and TBTU (3.74 mg) in NMP (1 mL) was added 4-fluoroaniline (1.73 mg) and followed DIPEA (5.43 µl). The mixture was stirred at room temperature for 16 hours. The mixture was diluted with MeOH and purified by preparative HPLC to give 1004 (3 mg).

| 1004 | |
|---|---|
| MS (M + H)⁺ Calcd. | 737.3 |
| MS (M + H)⁺ Observ. | 737.4 |
| Retention Time | 2.12 min |

| LC Condition | |
|---|---|
| Solvent A | 90% Water -10% Methanol-0.1% TFA |
| Solvent B | 10% Water -90% Methanol-0.1% TFA |
| Start % B | 30 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |
Preparation of Intermediate 2000
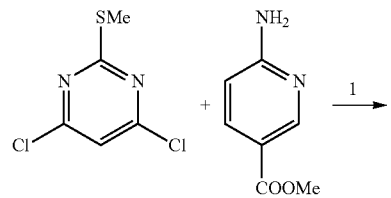
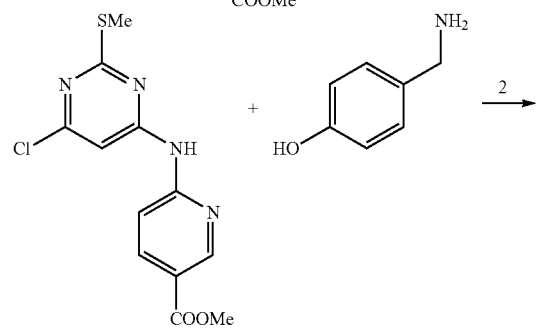
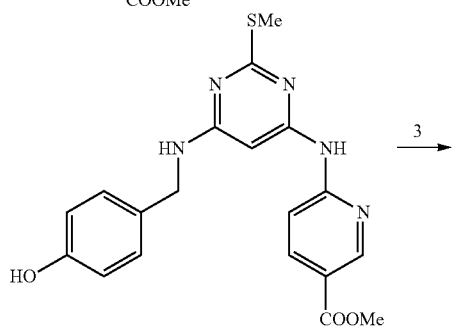
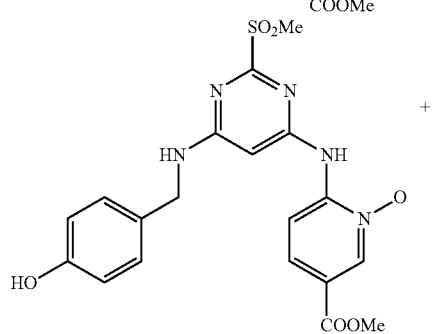
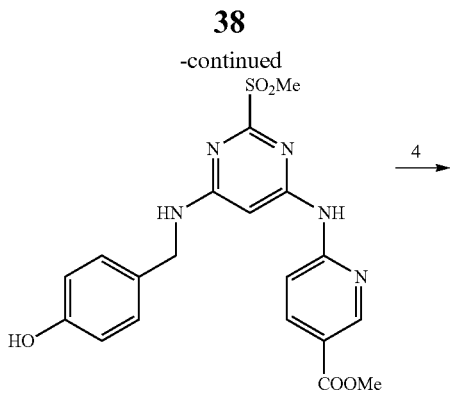
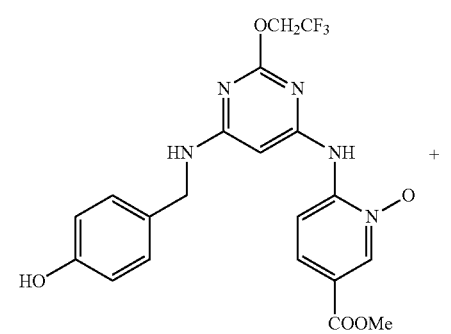
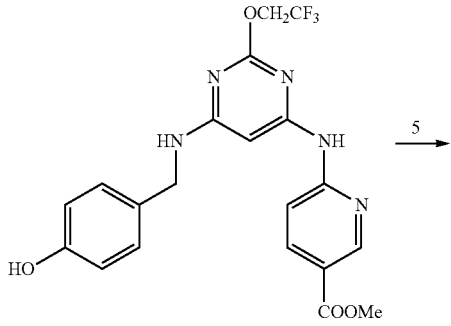
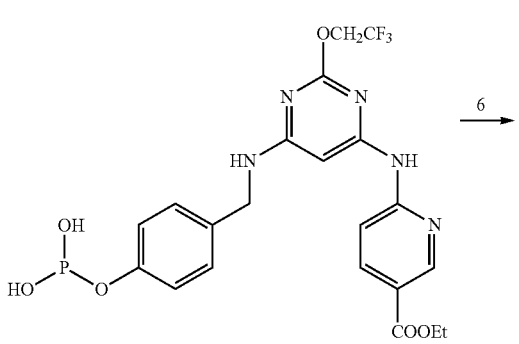
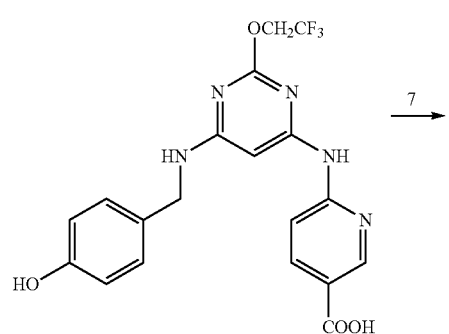

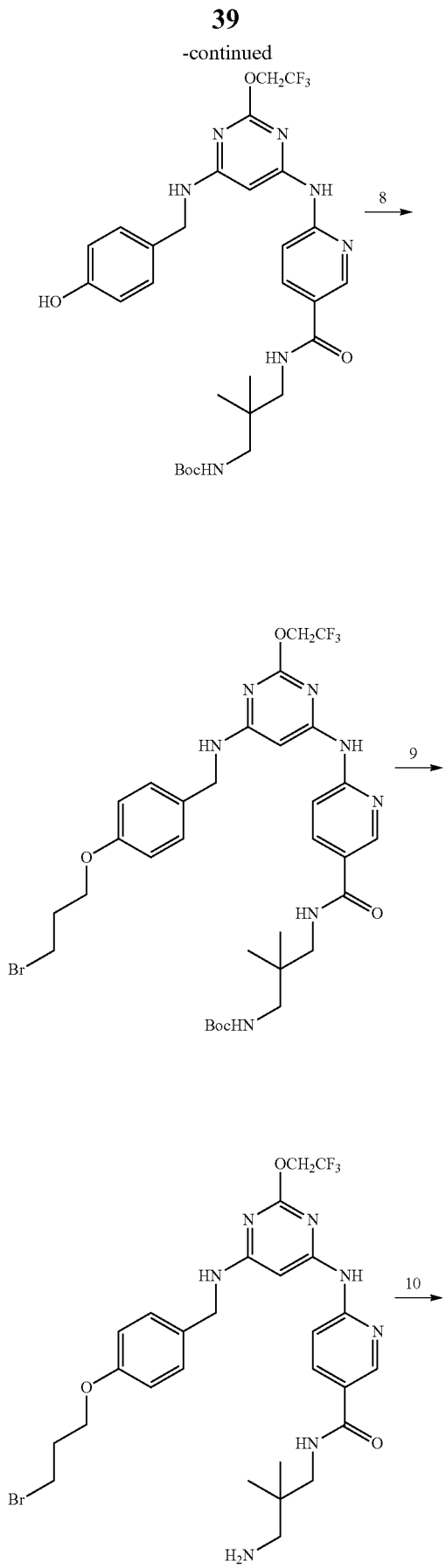

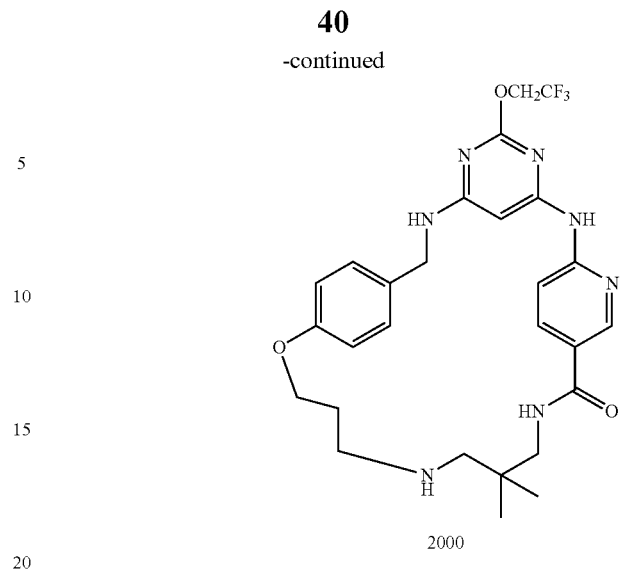

Step 1: NaHMDS (65.7 mL, 1M in THF) was added into the solution of 4,6-dichloro-2-(methylthio)pyrimidine (6.4 g) and methyl 4-aminobenzoate (5 g) in THF (200 mL). The reaction was stirred at room temperature for 16 hours, before being quenched by water. The aqueous layer was extracted with EtOAc (3×200 mL). The combined organic phase was dried over MgSO$_4$ and concentrated under vacuum to give the crude product, methyl 6-(6-chloro-2-(methylthio)pyrimidin-4-ylamino)nicotinate, which was used in the next step without purification.

| Methyl 6-(6-chloro-2-(methylthio)pyrimidin-4-ylamino)nicotinate | |
|---|---|
| MS (M + H)$^+$ Calcd. | 311.0 |
| MS (M + H)$^+$ Observ. | 311.1 |
| Retention Time | 1.83 minutes |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3u |

Step 2: iPr$_2$NEt was added into a solution of methyl 6-((6-chloro-2-(methylthio)pyrimidin-4-yl)amino)nicotinate (500 mg) and 4-(aminomethyl)phenol (238 mg) in dioxane (20 mL). The reaction was stirred at 115° C. for 16 hours, before being quenched by water. The aqueous layer was extracted with EtOAc (3×20 mL). The combined organic phase was dried over MgSO$_4$ and concentrated under vacuum to give the crude product which was used without purification.

| methyl 6-(6-(4-hydroxybenzylamino)-2-(methylthio)pyrimidin-4-ylamino)nicotinate | |
|---|---|
| MS (M + H)$^+$ Calcd. | 398.1 |
| MS (M + H)$^+$ Observ. | 398.3 |
| Retention Time | 1.60 minutes | methyl 6-(6-(4-hydroxybenzylamino)-2-(methylthio)pyrimidin-4-ylamino)nicotinate

| | LC Condition |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3u |

Step 3: mCPBA (1.02 g, 77%) was added into the solution of crude methyl 6-((6-((4-hydroxybenzyl)amino)-2-(methylthio)pyrimidin-4-yl)amino)nicotinate (0.9 g) in $CH_2Cl_2$ (10 mL). The reaction was stirred at room temperature for 2 hours to give 2-(6-(4-hydroxybenzylamino)-2-(methylsulfonyl)pyrimidin-4-ylamino)-5-(methoxycarbonyl)pyridine 1-oxide and methyl 6-(6-(4-hydroxybenzylamino)-2-(methylsulfonyl)pyrimidin-4-ylamino)nicotinate, before being quenched by water. The aqueous layer was extracted with EtOAc (3×20 mL). The combined organic phase was dried over $MgSO_4$ and concentrated under vacuum to give the crude product which was used as was.

2-(6-(4-hydroxybenzylamino)-2-(methylsulfonyl)pyrimidin-4-ylamino)-5-(methoxycarbonyl)pyridine 1-oxide

| | |
|---|---|
| MS (M + H)$^+$ Calcd. | 446.1 |
| MS (M + H)$^+$ Observ. | 446.1 |
| Retention Time | 1.57 min |
| | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um | methyl 6-(6-(4-hydroxybenzylamino)-2-(methylsulfonyl)-pyrimidin-4-ylamino)nicotinate

| | |
|---|---|
| MS (M + H)$^+$ Calcd. | 430.1 |
| MS (M + H)$^+$ Observ. | 430.1 |
| Retention Time | 1.66 min |
| | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Step 4: 2,2,2-trifluoroethanol (116 mg) and NaH (47 mg, 60%) were added into the solution of the crude products (50 mg) of Step 3 in THF (10 mL). The reaction was stirred at room temperature for 72 hours before being quenched by water. The aqueous layer was extracted with EtOAc (3×20 mL). The combined organic phase was dried over $MgSO_4$ and concentrated under vacuum to give a mixture of products, 2-(6-(4-hydroxybenzylamino)-2-(2,2,2-trifluoroethoxyl)pyrimidin-4-ylamino)-5-(methoxycarbonyl)pyridine 1-oxide and methyl 6-(6-(4-hydroxybenzylamino)-2-(2,2,2-trifluoroethoxyl)pyrimidin-4-ylamino)nicotinate, which was used as was.

2-(6-(4-hydroxybenzylamino)-2-(2,2,2-trifluoroethoxy)pyrimidin-4-ylamino)-5-(methoxycarbonyl)pyridine 1-oxide

| | |
|---|---|
| MS (M + H)$^+$ Calcd. | 466.1 |
| MS (M + H)$^+$ Observ. | 466.1 |
| Retention Time | 2.04 min |
| | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um | methyl 6-(6-(4-hydroxybenzylamino)-2-(2,2,2-trifluoroethoxy)-pyrimidin-4-ylamino)nicotinate

| | |
|---|---|
| MS (M + H)$^+$ Calcd. | 450.1 |
| MS (M + H)$^+$ Observ. | 450.1 |
| Retention Time | 1.85 min |
| | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Step 5: $PCl_3$ (764 mg) was added into the solution of the crude mixture (1 g) from Step 4 in EtOAc. The reaction was stirred for 30 minutes, before being quenched by $NaHCO_3$. After solvents were removed under vacuum, the residue containing methyl 6-(6-(4-(phosphonooxy)benzylamino)-2-(2,2,2-trifluoroethoxyl)pyrimidin-4-ylamino)nicotinate and methyl 6-(6-(4-hydroxybenzylamino)-2-(2,2,2-trifluoroethoxyl)pyrimidin-4-ylamino)nicotinate was used as was.

methyl 6-(6-(4-(phosphonooxy)benzylamino)-2-(2,2,2-trifluoroethoxy)pyrimidin-4-ylamino)nicotinate

| | |
|---|---|
| MS (M + H)$^+$ Calcd. | 514.1 |
| MS (M + H)$^+$ Observ. | 514.1 |
| Retention Time | 1.82 min |
| | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Step 6: $K_2CO_3$ (5 g) was added into the solution of the whole crude mixture of Step 6 in MeOH (10 mL) and water (10 mL). The reaction was run at room temperature for 72 hours. Methanol was removed under vacuum. The aqueous layer was extracted with EtOAc (3×100 mL). The combined organic phase was dried over MgSO$_4$ and concentrated under vacuum to give the crude 6-(6-(4-hydroxybenzylamino)-2-(2,2,2-trifluoroethoxyl)pyrimidin-4-ylamino)nicotinic acid which will be used without purification.

| 6-(6-(4-hydroxybenzylamino)-2-(2,2,2-trifluoroethoxy)-pyrimidin-4-ylamino)nicotinic acid | |
|---|---|
| MS (M + H)$^+$ Calcd. | 436.1 |
| MS (M + H)$^+$ Observ. | 436.1 |
| Retention Time | 1.75 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Step 7: iPr$_2$NEt (0.5 mL) was added into a solution of 6-((6-((4-hydroxybenzyl)amino)-2-(2,2,2-trifluoroethoxyl)pyrimidin-4-yl)amino)nicotinic acid (340 mg), tert-butyl(3-amino-2,2-dimethylpropyl)carbamate (316 mg) and TBTU (501 mg) in THF (10 mL). The reaction was stirred at room temperature for 16 hours before being quenched by water (10 mL). The aqueous layer was extracted with EtOAc (3×10 mL). The combined organic phase was dried over MgSO$_4$ and concentrated under vacuum to give the crude product, tert-butyl 3-(6-(6-(4-hydroxybenzylamino)-2-(2,2,2-trifluoroethoxyl)pyrimidin-4-ylamino)nicotinamido)-2,2-dimethylpropylcarbamate, which was purified by silica gel chromatography.

| tert-butyl 3-(6-(6-(4-hydroxybenzylamino)-2-(2,2,2-trifluoroethoxy)pyrimidin-4-ylamino)nicotinamido)-2,2-dimethylpropylcarbamate | |
|---|---|
| MS (M + H)$^+$ Calcd. | 620.3 |
| MS (M + H)$^+$ Observ. | 620.3 |
| Retention Time | 2.09 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Step 8: A suspension of tert-butyl(3-(6-((6-((4-hydroxybenzyl)amino)-2-(2,2,2-trifluoroethoxyl)pyrimidin-4-yl)amino)nicotinamido)-2,2-dimethylpropyl)carbamate (30 mg), 1,3-dibromopropane (14.7 mg) and K$_2$CO$_3$ (13.4 mg) in acetone (6 mL) was heated to reflux for 16 hours. The mixture was diluted with EtOAc (200 mL), washed with water (30 mL), brine (30 mL), dried over MgSO$_4$ and concentrated. The residue was purified by preparative HPLC to give desired product tert-butyl 3-(6-(6-(4-(3-bromopropoxy)benzylamino)-2-(2,2,2-trifluoroethoxy)pyrimidin-4-ylamino)nicotinamido)-2,2-dimethylpropylcarbamate (11 mg).

| tert-butyl 3-(6-(6-(4-(3-bromopropoxy)benzylamino)-2-(2,2,2-trifluoroethoxy)pyrimidin-4-ylamino)nicotinamido)-2,2-dimethylpropylcarbamate | |
|---|---|
| MS (M + H)$^+$ Calcd. | 740.2 |
| MS (M + H)$^+$ Observ. | 740.3 |
| Retention Time | 1.94 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Step 9: To a solution of tert-butyl(3-(6-((6-((4-(3-bromopropoxyl)benzyl)amino)-2-(2,2,2-trifluoroethoxyl)pyrimidin-4-yl)amino)nicotinamido)-2,2-dimethylpropyl)carbamate (10 mg) in DCM (3 mL) was added TFA (0.3 ml). The mixture was stirred at room temperature for 3 hours. All the solvents were removed under vacuum to give N-(3-amino-2,2-dimethylpropyl)-6-(6-(4-(3-bromopropoxyl)benzylamino)-2-(2,2,2-trifluoroethoxyl)pyrimidin-4-ylamino)nicotinamide (8 mg).

| N-(3-amino-2,2-dimethylpropyl)-6-(6-(4-(3-bromopropoxy)-benzylamino)-2-(2,2,2-trifluoroethoxy)pyrimidin-4-ylamino)-nicotinamide | |
|---|---|
| MS (M + H)$^+$ Calcd. | 640.2 |
| MS (M + H)$^+$ Observ. | 640.2 |
| Retention Time | 1.19 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Step 10: A mixture of N-(3-amino-2,2-dimethylpropyl)-6-((6-((4-(3-bromopropoxyl)benzyl)amino)-2-(2,2,2-trifluoroethoxyl)pyrimidin-4-yl)amino)nicotinamide (8 mg) and NaHCO$_3$ (1.05 mg) in MeCN (5 mL) was heated at 85° C. in a sealed tube for 16 hours. The solvent was removed under vacuum. The residue was purified by preparative HPLC to give 1003 (4 mg).

| 2000 | |
|---|---|
| MS (M + H)$^+$ Calcd. | 560.3 |
| MS (M + H)$^+$ Observ. | 560.3 |
| Retention Time | 1.36 min |
| LC Condition | |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Compound 2001

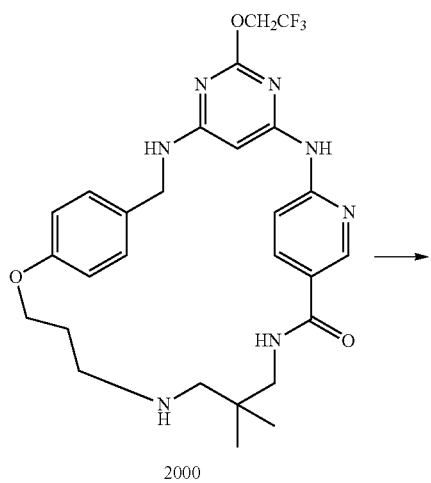

2000

2001

To a solution of Compound 2000 (21 mg) in THF (10 mL) was added methyl 2-chloro-2-oxoacetate (55.2 mg) and iPr$_2$NEt (0.098 mL). The mixture was stirred at room temperature for 4 hours. All the solvents were removed under vacuum. The residue was purified by preparative HPLC to give Compound 2001.

| | 2001 |
|---|---|
| MS (M + H)$^+$ Calcd. | 732.3 |
| MS (M + H)$^+$ Observ. | 732.1 |
| Retention Time | 1.66 min |
| LC Condition | |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Compound 2002

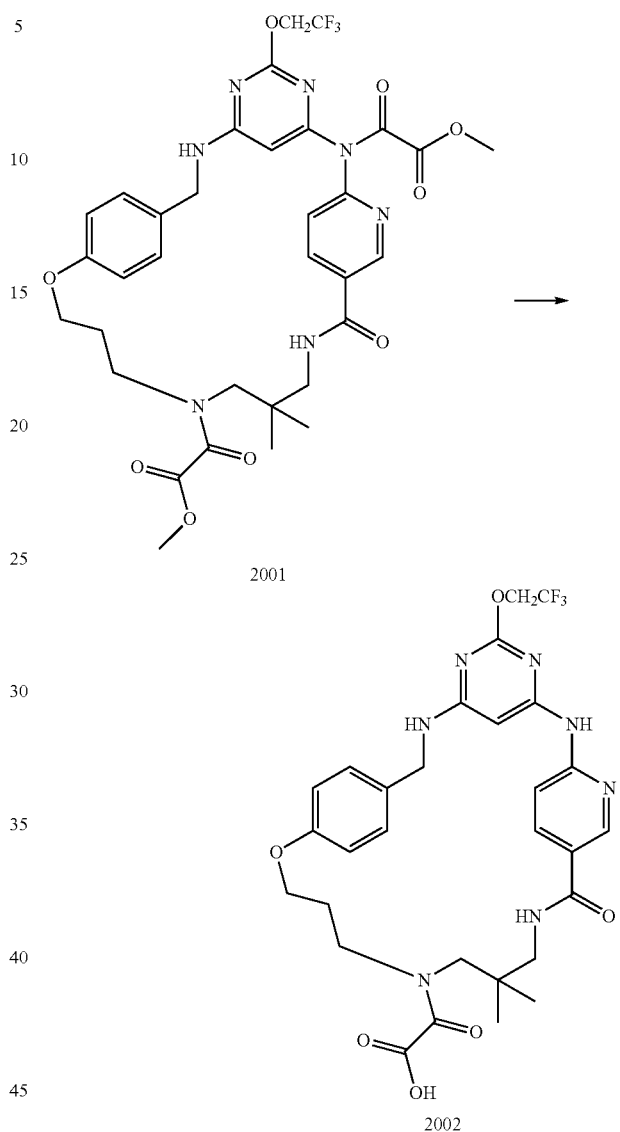

2001

2002

To a solution of Compound 2001 (25 mg) in acetone (3 mL) was added a solution of K$_2$CO$_3$ (53.5 mg) in water (3.00 mL). The mixture was stirred at room temperature for 16 hours. The mixture was acidified by 1 N HCl to pH ~3 and extracted with EtOAc (2×30 mL). The organic layers were combined, washed with brine (30 mL), dried over MgSO$_4$ and concentrated to give Compound 2002 (20 mg).

| | 2002 |
|---|---|
| MS (M + H)$^+$ Calcd. | 632.2 |
| MS (M + H)$^+$ Observ. | 632.1 |
| Retention Time | 1.54 min |
| LC Condition | |
| Solvent A | 90% Water-10% Methanol-0.1% TFA |
| Solvent B | 10% Water-90% Methanol-0.1% TFA |
| Start % B | 30 |
| Final % B | 100 |

| 2002 | |
|---|---|
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Compound 2003

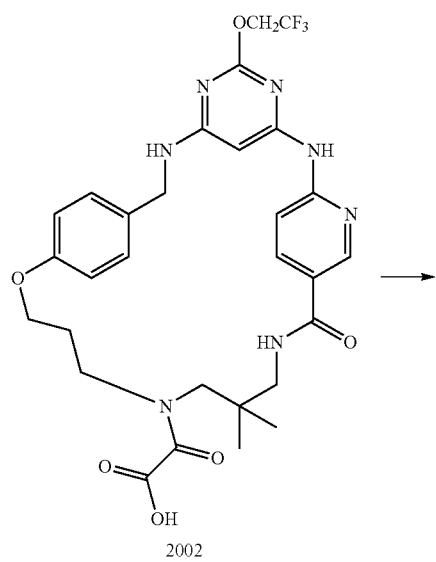

2002

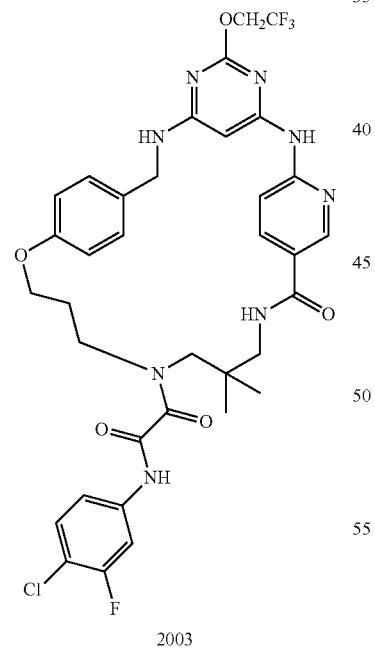

2003

To a solution of Compound 2002 (10 mg) and TBTU (10.17 mg) in DMF (1.5 mL) was added 4-chloro-3-fluoroaniline (6.91 mg), followed by iPr₂NEt (0.011 mL). The mixture was stirred at room temperature for 16 hours. The mixture was diluted with MeOH and purified by preparative HPLC to give Compound 2003 (5.3 mg).

| 2003 | |
|---|---|
| MS (M + H)⁺ Calcd. | 759.2 |
| MS (M + H)⁺ Observ. | 759.1 |
| Retention Time | 2.17 min |
| | LC Condition |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Compound 2004

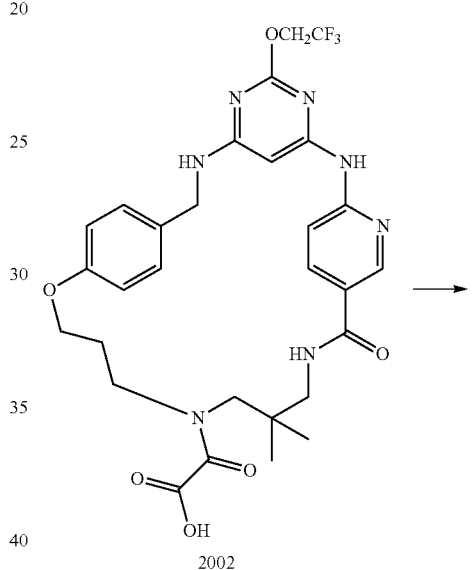

2002

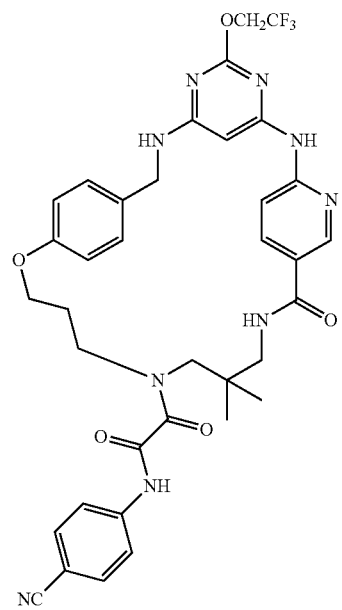

2004

To a solution of Compound 2002 (10 mg) and TBTU (10.17 mg) in DMF (1.5 mL) was added 4-aminobenzonitrile (5.61 mg), followed by iPr₂NEt (0.011 mL). The mixture was stirred at room temperature for 16 hours. The mixture was purified by preparative HPLC to give Compound 2003 (3 mg).

| | 2004 |
|---|---|
| MS (M + H)⁺ Calcd. | 732.3 |
| MS (M + H)⁺ Observ. | 732.1 |
| Retention Time | 1.95 min |
| | LC Condition |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Intermediate 3000

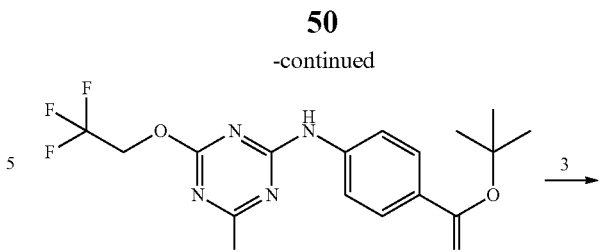

-continued

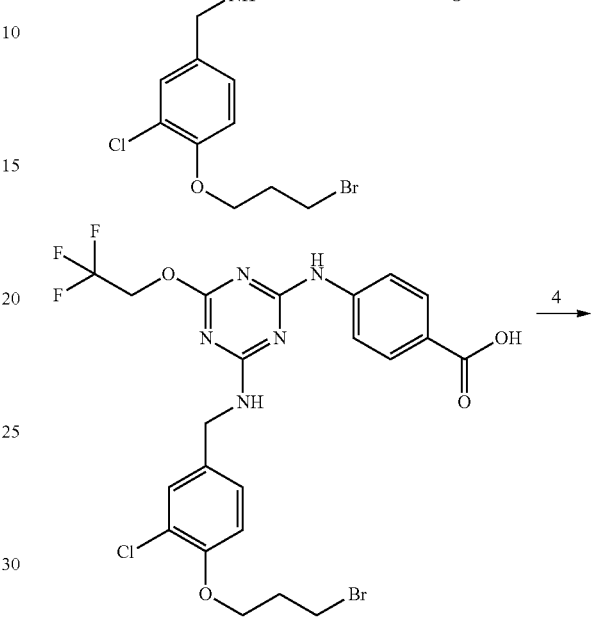

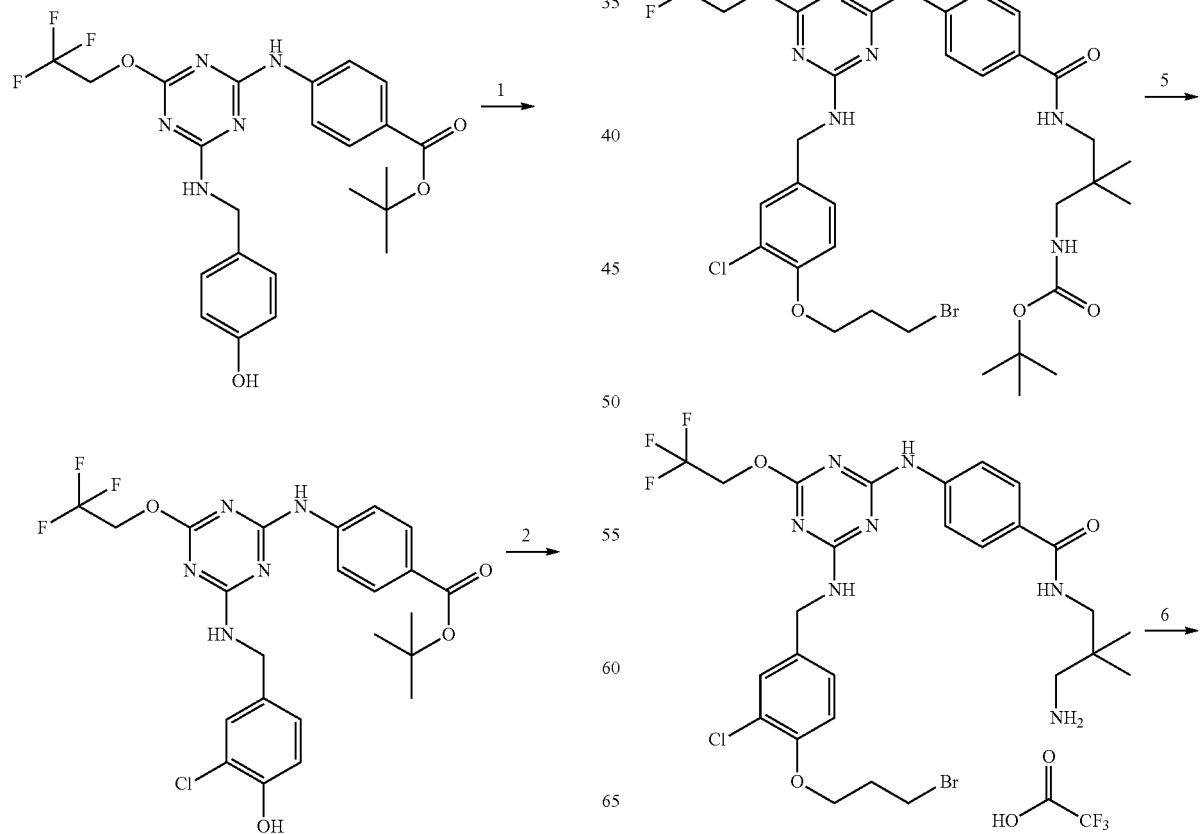

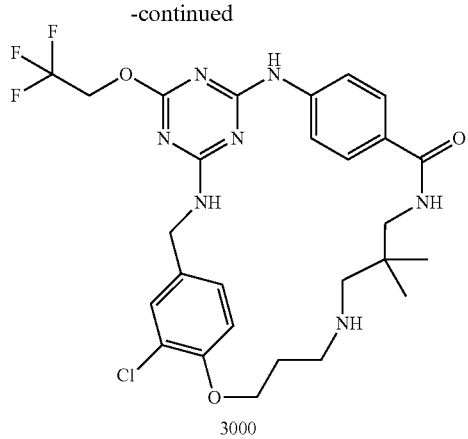

3000

Step 1: To a 100 mL round-bottom flask equipped with a stir bar was added 4-(aminomethyl)-2-chlorophenol hydrobromide (1.34 g, 5.63 mmol), tert-butyl 4-((4-chloro-6-(2,2,2-trifluoroethoxy)-1,3,5-triazin-2-yl)amino)benzoate (3.00 g, 5.63 mmol) and THF (28 mL). To the solution was added N,N-diisopropylethylamine (2.95 ml, 16.9 mmol). The mixture was stirred at room temperature for 3 days. The mixture was concentrated in vacuo and the resulting residue was subjected to C$_{18}$ chromatography (water:methanol 1:1 to methanol) to afford tert-butyl 4-((4-((3-chloro-4-hydroxybenzyl)amino)-6-(2,2,2-trifluoroethoxy)-1,3,5-triazin-2-yl)amino)benzoate as a colorless solid (2.88 g, 90%). MS m/z=526.3 (M+H)$^+$.

Step 2: To a dry 30 mL vial equipped with a stir bar was added tert-butyl 4-((4-((3-chloro-4-hydroxybenzyl)amino)-6-(2,2,2-trifluoroethoxy)-1,3,5-triazin-2-yl)amino)benzoate (1.80 g, 3.18 mmol), potassium carbonate (1.32 g, 9.55 mmol) and acetone (16 mL). To the mixture was added 1,3-dibromopropane (3.37 ml, 25.5 mmol). The vial was placed in a 60° C. heating block with stirring for 2.5 h. The mixture was cooled to room temperature and then concentrated in vacuo. The resulting solid residue was subjected to SiO$_2$ chromatography (hexanes:EtOAc 85:15 to 75:25) to afford tert-butyl 4-((4-((4-(3-bromopropoxy)-3-chlorobenzyl)amino)-6-(2,2,2-trifluoroethoxy)-1,3,5-triazin-2-yl)amino)benzoate as a colorless solid (1.60 g, 78%). MS m/z=646.25 (M+H)$^+$.

Step 3: To a 100 mL round-bottom flask equipped with a stir bar and charged with tert-butyl 4-((4-((4-(3-bromopropoxy)-3-chlorobenzyl)amino)-6-(2,2,2-trifluoroethoxy)-1,3,5-triazin-2-yl)amino)benzoate (8.42 g, 13.0 mmol) in CH$_2$Cl$_2$ (15 mL) was added trifluoroacetic acid (15.0 mL, 195 mmol). The solution was stirred at room temperature for 2 h. The solution was diluted with toluene (20 mL) and then concentrated in vacuo to afford crude 4-((4-((4-(3-bromopropoxy)-3-chlorobenzyl)amino)-6-(2,2,2-trifluoroethoxy)-1,3,5-triazin-2-yl)amino)benzoic acid as a solid foam.

Step 4: To a 100 mL round-bottom flask charged with the 4-((4-((4-(3-bromopropoxy)-3-chlorobenzyl)amino)-6-(2,2,2-trifluoroethoxy)-1,3,5-triazin-2-yl)amino)benzoic acid prepared above (13.0 mmol) was added CH$_2$Cl$_2$ (65 mL), and then N,N-diisopropylethylamine (7.95 mL, 45.5 mmol). The flask was cooled with a 0° C. bath. To the solution was added tert-butyl(3-amino-2,2-dimethylpropyl)carbamate (3.16 g, 15.6 mmol), and then O-(7-azabenzotriazol-1-yl)-N,N,N',N'-tetramethyluronium hexafluorophosphate (HATU, 6.43 g, 16.9 mmol). The bath was removed and the solution was allowed to warm to room temperature with stirring for 1 h. The solution was transferred to a 1 L separatory funnel and was diluted with EtOAc (500 mL). The solution was washed with aq. 2M HCl (2×100 mL), and then with sat. aq. NaHCO$_3$ (100 mL), and then with sat. aq. NaCl (100 mL). The organic solution was dried over MgSO$_4$; filtered; and then concentrated in vacuo. The resulting solid residue was subjected to SiO$_2$ chromatography (hexanes:EtOAc, 1:1) to afford tert-butyl(3-(4-((4-((4-(3-bromopropoxy)-3-chlorobenzyl)amino)-6-(2,2,2-trifluoroethoxy)-1,3,5-triazin-2-yl)amino)benzamido)-2,2-dimethylpropyl)carbamate as a colorless solid (8.77 g, 81%). $^1$H NMR (400 MHz, CDCl$_3$) δ 7.89 (d, J=8.5 Hz, 2H), 7.76-7.66 (m, 1H), 7.62 (dd, J=15.6, 8.5 Hz, 2H), 7.35 (s, 1H), 7.22-7.15 (m, 1H), 6.96-6.89 (m, 1H), 5.16-5.04 (m, 1H), 4.73 (dq, J=12.2, 8.4 Hz, 2H), 4.57 (d, J=5.3 Hz, 2H), 4.19-4.14 (m, 2H), 3.69-3.61 (m, 2H), 3.28-3.18 (m, 2H), 3.00-2.92 (m, 2H), 2.36 (sxt, J=5.8 Hz, 2H), 1.46 (d, J=2.0 Hz, 9H), 0.91 (d, J=3.3 Hz, 6H); MS m/z=774.25 (M+1)$^+$.

Step 5: To a 100 mL round-bottom flask equipped with a stir bar and charged with tert-butyl(3-(4-((4-((4-(3-bromopropoxy)-3-chlorobenzyl)amino)-6-(2,2,2-trifluoroethoxy)-1,3,5-triazin-2-yl)amino)benzamido)-2,2-dimethylpropyl)carbamate (1.655 g, 2.136 mmol) was added CH$_2$Cl$_2$ (5 mL), and then trifluoroacetic acid (2.50 mL, 32.4 mmol). The solution was stirred at room temperature for 2 h. The solution was transferred to a 250 mL separatory funnel and was diluted with EtOAc (75 mL). The solution was washed with sat. aq. NaHCO$_3$ (75 mL). The aq. phase was extracted with EtOAc (2×75 mL). The combined organics were washed with sat. aq. NaCl (50 mL); dried over MgSO4; filtered; then concentrated in vacuo to afford N-(3-amino-2,2-dimethylpropyl)-4-((4-((4-(3-bromopropoxy)-3-chlorobenzyl)amino)-6-(2,2,2-trifluoroethoxy)-1,3,5-triazin-2-yl)amino)benzamide trifluoroacetic acid as a colorless solid (1.52 g, 100%). MS m/z=674.25 (M+1)$^+$.

Step 6: To a dry 500 mL round-bottom flask equipped with a large stir bar and charged with N-(3-amino-2,2-dimethylpropyl)-4-((4-((4-(3-bromopropoxy)-3-chlorobenzyl)amino)-6-(2,2,2-trifluoroethoxy)-1,3,5-triazin-2-yl)amino)benzamide trifluoroacetic acid (7.461 g, 11.05 mmol) in Acetonitrile (315 ml) was added potassium carbonate (5.2 g, 38 mmol). The flask was fitted with a water-cooled reflux and the mixture was then stirred at reflux for 3 h. The mixture was concentrated in vacuo and the white solid residue was treated with CH$_2$Cl$_2$:MeOH (1:1, 500 mL) and vigorously agitated. The mixture was filtered and the filter cake was extracted with CH$_2$Cl:MeOH (1:1, 200 mL). The combined filtrate was concentrated in vacuo and the resulting white solid was triturated with MeOH (15 mL) to afford crude Compound 1001 as a white solid powder, 4.636 g (52%). A portion of the material was further purified by HPLC as follows: Column=Waters XBridge C18, 19×200 mm, 5-μm particles; Guard Column=Waters) (Bridge C18, 19×10 mm, 5-μm particles; Mobile Phase A=water with 20-mM ammonium acetate; Mobile Phase B=95:5 acetonitrile:water with 20-mM ammonium acetate; Gradient=20-100% B over 18 minutes, then a 4-minute hold at 100% B; Flow=20 mL/min. Fractions containing the desired product were combined and dried via centrifugal evaporation to afford pure Intermediate 3000. $^1$H NMR (500 MHz, DMSO-d$_6$) δ 9.86 (s, 1H), 8.59 (t, J=5.2 Hz, 1H), 8.40 (t, J=5.6 Hz, 1H), 7.37-7.31 (m, 3H), 7.28-7.24 (m, 1H), 7.20 (d, J=1.8 Hz, 1H), 7.14 (d, J=8.9 Hz, 2H), 4.98 (q, J=9.2 Hz, 2H), 4.37 (d, J=5.5 Hz, 2H), 4.26 (t, J=6.3 Hz, 2H), 3.20 (d, J=5.2 Hz, 2H), 2.67 (t, J=6.3 Hz, 2H), 2.40 (s, 2H), 1.79 (t, J=6.4 Hz, 2H), 1.73 (s, 1H), 0.89 (s, 6H); MS m/z=594.3 (M+1)$^+$.

Preparation of Compound 3001

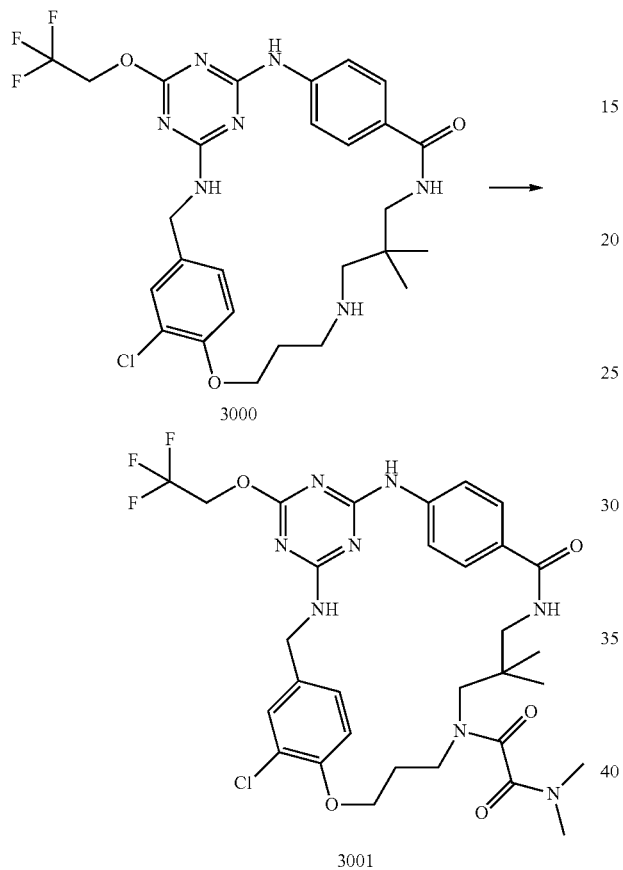

To a 2 dram vial equipped with a stir bar was added Compound 3000 (15 mg, 0.025 mmol) and 2-(dimethylamino)-2-oxoacetic acid (3.0 mg, 0.025 mmol). To the vial was added DMF (250 μL) and N,N-diisopropylethylamine (8.8 μL, 0.050 mmol). To the solution was added O-(7-azabenzotriazol-1-yl)-N,N,N',N'-Tetramethyluronium hexafluorophosphate (HATU, 11 mg, 0.028 mmol). The orange solution was stirred for 45 min. The solution was then directly purified by HPLC as follows: Column=Waters XBridge C18, 19×200 mm, 5-μm particles; Guard Column=Waters XBridge C18, 19×10 mm, 5-μm particles; Mobile Phase A=water with 20-mM ammonium acetate; Mobile Phase B=95:5 acetonitrile:water with 20-mM ammonium acetate; Gradient=30-100% B over 20 minutes, then a 4-minute hold at 100% B; Flow=20 mL/min. Fractions containing the desired product were combined and dried via centrifugal evaporation to afford Compound 3001 as a white solid (8 mg, 45%). $^1$H NMR (500 MHz, DMSO-d$_6$) δ 9.91 (s, 1H), 8.43-8.39 (m, 1H), 8.27 (t, J=6.3 Hz, 1H), 7.53-7.46 (m, 4H), 7.33-7.26 (m, 3H), 7.25-7.21 (m, 1H), 5.00 (q, J=8.9 Hz, 2H), 4.43 (d, J=5.5 Hz, 2H), 4.11 (t, J=6.7 Hz, 2H), 3.39 (t, J=6.9 Hz, 2H), 3.29 (s, 2H), 3.19 (d, J=6.4 Hz, 2H), 2.97 (s, 3H), 2.92 (s, 3H), 1.91 (quin, J=6.9 Hz, 2H), 0.95 (s, 6H); MS m/z=693.3 (M+1)$^+$.

Preparation of Compounds 3002-30xx, a general procedure: To a solution of amine (1 eq.), 2-amino-2-oxoacetic acid (1.18 eq.) and HCTU (1.18 eq.) in DMF (1.5 mL) was added iPr$_2$NEt (4 eq.). The mixture was stirred at room temperature for 3 hours. The mixture was purified by preparative HPLC.

| LC Condition | |
|---|---|
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

| Compd.# | Structure | Rf (min.) | (M + H)$^+$ Caculd. | (M + H)$^+$ Observ. |
|---|---|---|---|---|
| 3002 | 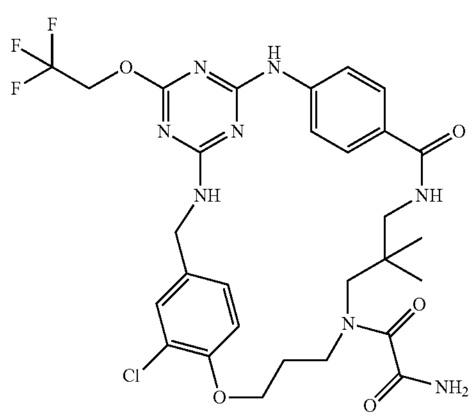 [SMILES: CC1(C)CNC(=O)c2ccc(cc2)Nc2nc(nc(OCC(F)(F)F)n2)NCc2ccc(c(Cl)c2)OCCCN(C(=O)C(N)=O)C1] | 1.70 | 665.2 | 665.3 |

-continued
| Compd.# | Structure | Rf (min.) | (M + H)+ Caculd. | (M + H)+ Observ. |
|---|---|---|---|---|
| 3003 | 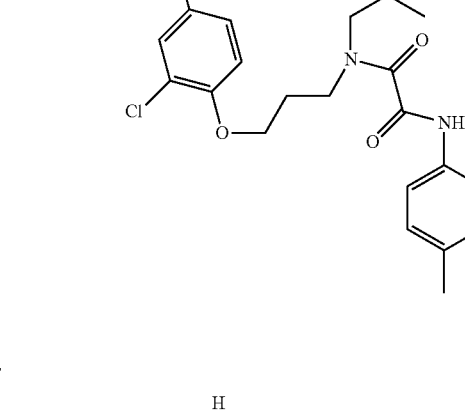 | 2.13 | 755.3 | 755.4 |
| 3004 | 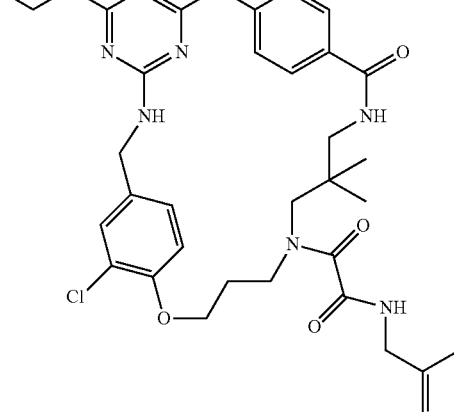 | 2.05 | 773.3 | 773.4 |
| 3005 | 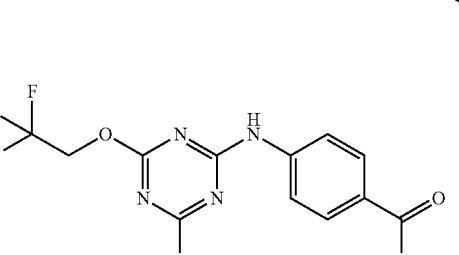 | 1.81 | 735.3 | 735.4 |

| Compd.# | Structure | Rf (min.) | (M + H)+ Caculd. | (M + H)+ Observ. |
|---|---|---|---|---|
| 3006 | 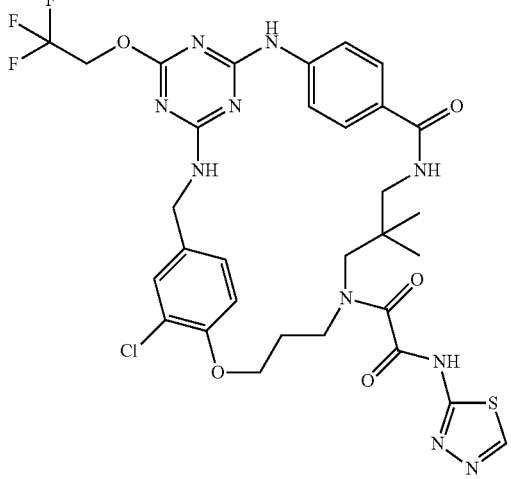 | 1.89 | 749.2 | 749.3 |
| 3007 | 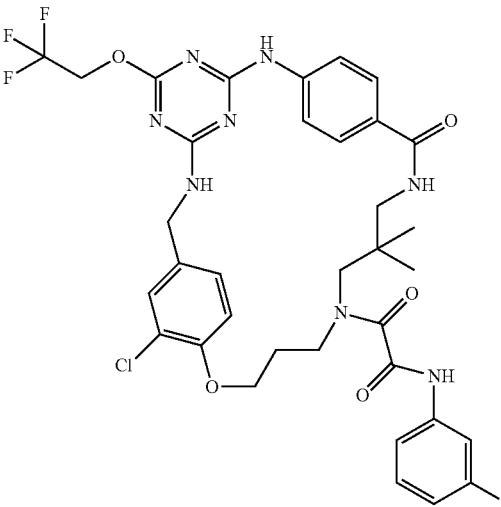 | 2.16 | 759.2 | 759.4 |
| 3008 | 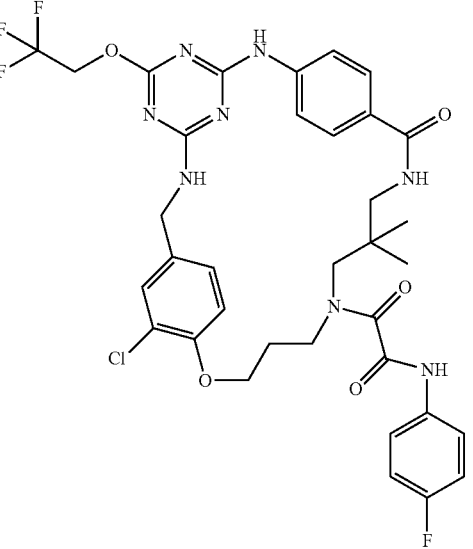 [SMILES: CC1(C)CNC(=O)c2ccc(cc2)Nc2nc(nc(OCC(F)(F)F)n2)NCc2ccc(c(Cl)c2)OCCCN(C(=O)C(=O)Nc2ccc(F)cc2)C1] | 2.13 | 759.2 | 759.4 |

| Compd.# | Structure | Rf (min.) | (M + H)+ Caculd. | (M + H)+ Observ. |
|---|---|---|---|---|
| 3009 | 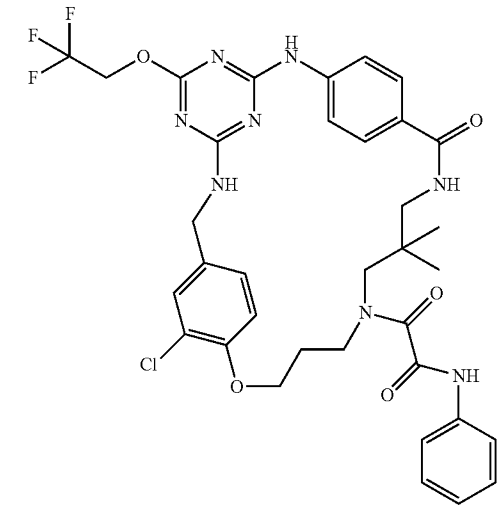 [SMILES: CC1(C)CNC(=O)c2ccc(cc2)Nc2nc(nc(OCC(F)(F)F)n2)NCc2ccc(c(Cl)c2)OCCCN(C(=O)C(=O)Nc2ccccc2)C1] | 2.07 | 741.2 | 741.4 |
| 3010 | 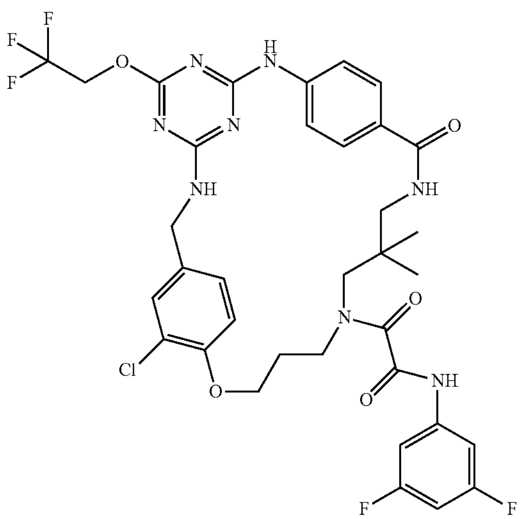 [SMILES: CC1(C)CNC(=O)c2ccc(cc2)Nc2nc(nc(OCC(F)(F)F)n2)NCc2ccc(c(Cl)c2)OCCCN(C(=O)C(=O)Nc2cc(F)cc(F)c2)C1] | 2.26 | 777.2 | 777.4 |
| 3011 | 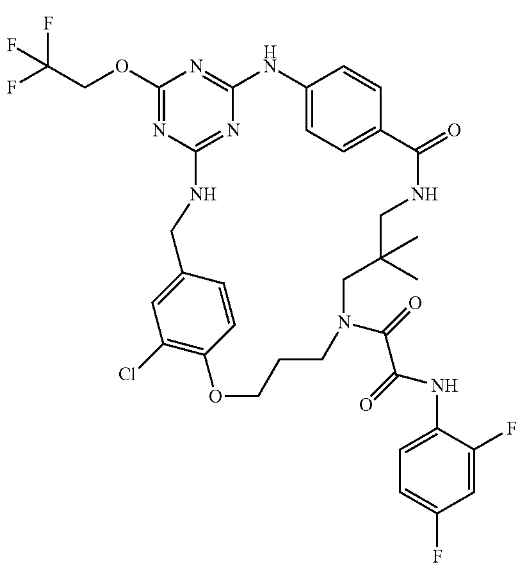 [SMILES: CC1(C)CNC(=O)c2ccc(cc2)Nc2nc(nc(OCC(F)(F)F)n2)NCc2ccc(c(Cl)c2)OCCCN(C(=O)C(=O)Nc2ccc(F)cc2F)C1] | 2.13 | 777.2 | 777.4 |

| Compd.# | Structure | Rf (min.) | (M + H)+ Caculd. | (M + H)+ Observ. |
|---|---|---|---|---|
| 3012 | 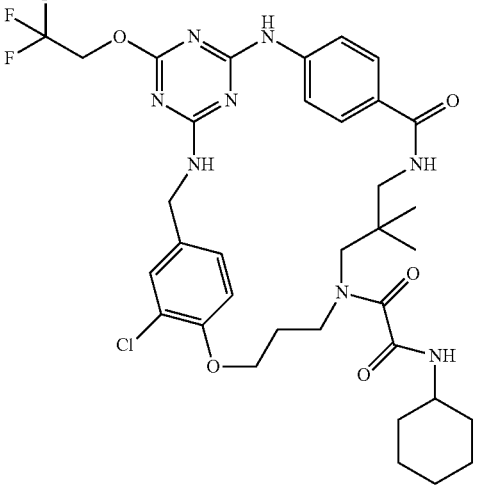 | 2.13 | 747.3 | 747.5 |
| 3013 | 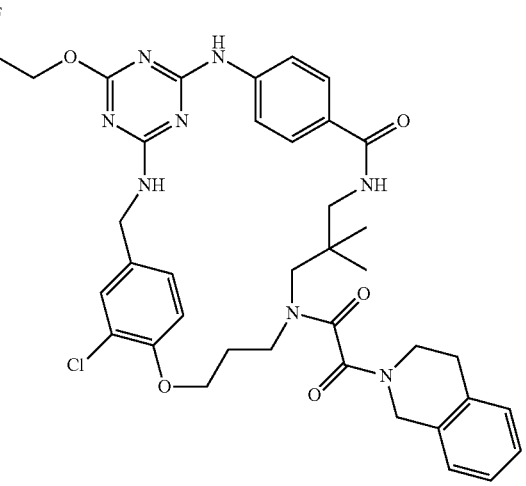 | 2.07 | 781.3 | 781.5 |
| 3014 | 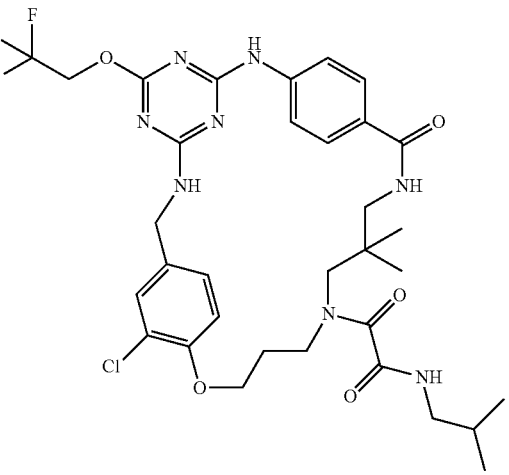 | 2.02 | 721.3 | 721.4 |

-continued
| Compd.# | Structure | Rf (min.) | (M + H)+ Caculd. | (M + H)+ Observ. |
|---|---|---|---|---|
| 3015 | 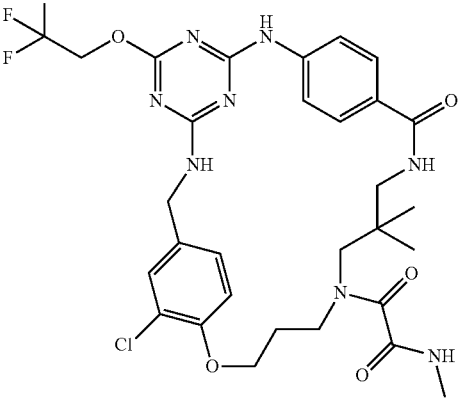 | 1.78 | 679.2 | 679.3 |
| 3016 | 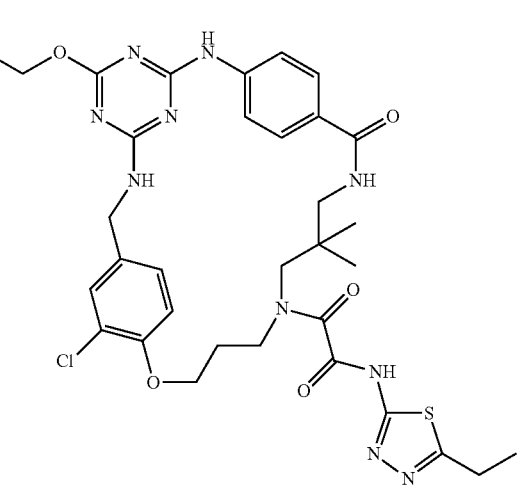 | 2.03 | 777.2 | 777.4 |
| 3017 | 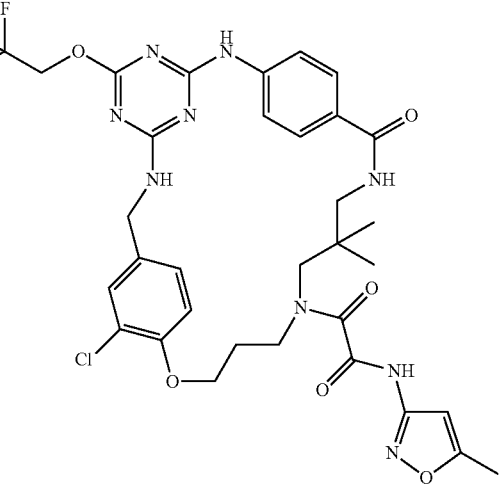 | 1.93 | 746.2 | 746.4 |

-continued

| Compd.# | Structure | Rf (min.) | (M + H)+ Caculd. | (M + H)+ Observ. |
|---|---|---|---|---|
| 3018 | 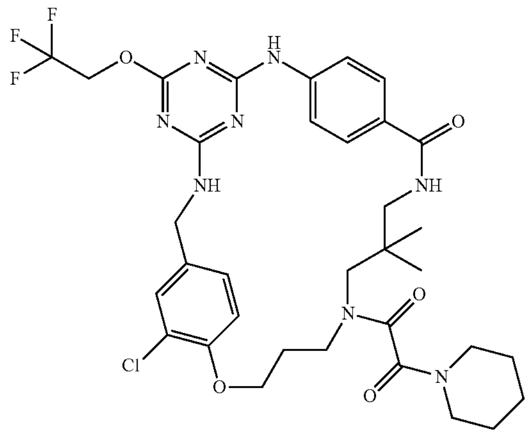 [SMILES: CC1(C)CNC(=O)c2ccc(cc2)Nc2nc(nc(OCC(F)(F)F)n2)NCc2ccc(c(Cl)c2)OCCCN(C(=O)C(=O)N2CCCCC2)C1] | 1.96 | 733.3 | 733.4 |
| 3019 | 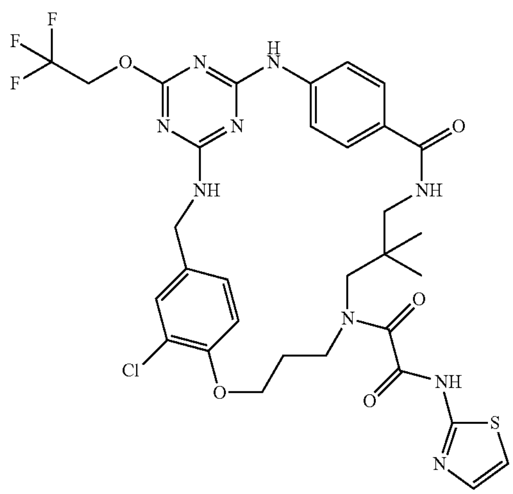 [SMILES: CC1(C)CNC(=O)c2ccc(cc2)Nc2nc(nc(OCC(F)(F)F)n2)NCc2ccc(c(Cl)c2)OCCCN(C(=O)C(=O)Nc2nccs2)C1] | 2.01 | 748.2 | 748.3 |
| 3020 | 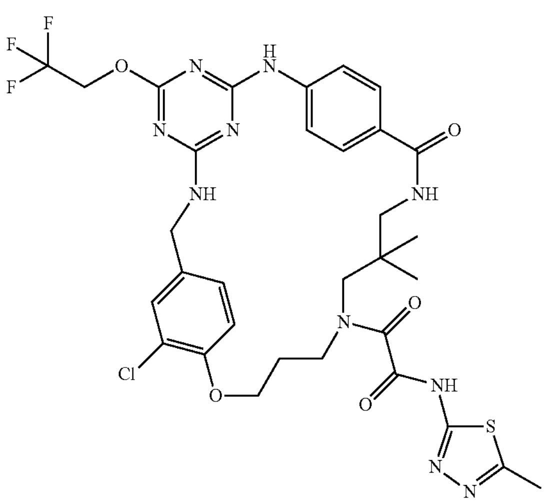 [SMILES: Cc1nnc(NC(=O)C(=O)N2CCCOc3ccc(cc3Cl)CNc3nc(nc(OCC(F)(F)F)n3)Nc3ccc(cc3)C(=O)NCC(C)(C)C2)s1] | 1.94 | 763.2 | 763.3 |

We claim:
1. A compound of formula I

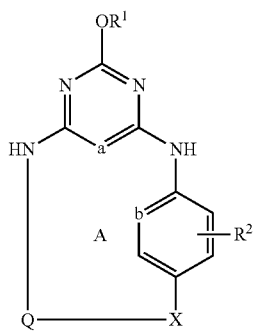

a is C or N;
b is C or N;
R¹ is alkyl, hydroxyalkyl, alkoxyalkyl, haloalkyl, cycloalkyl, hydroxycycloalkyl, alkoxycycloalkyl, halocycloalkyl, cycloalkenyl, benzyl, indanyl, or alkylcarbonyl;
R² is hydrogen, cyano, halo, alkyl, haloalkyl, alkoxy, or haloalkoxy;
R³ is hydrogen, alkyl, alkylcarbonyl, alkoxycarbonyl, benzyloxycarbonyl, aminocarbonyl, alkylaminocarbonyl, or dialkyaminocarbonyl;
R⁴ is hydrogen or alkyl;
R⁵ is hydrogen or alkyl;
R⁶ is hydrogen, alkyl, (cycloalkyl)alkyl, (Ar¹)alkyl, cycloalkyl, (alkyl)cycloalkyl, tetralinyl, or Ar¹;
R⁷ is hydrogen or alkyl;
or R⁶ and R⁷ taken together with the nitrogen to which they are attached is azetidinyl, pyrrolidinyl, piperidinyl, piperazinyl, or morpholinyl, and is substituted with 0-3 substituents selected from hydroxy, alkyl, alkylcarbonyl, and alkoxycarbonyl;
Q is an alkylene or alkenylene chain containing 0-6 groups selected from the group consisting of O, NR³, S, S(O), S(O₂), C(O)O, C(O)NR⁴, OC(O)NR⁴, NR⁴C(O)NR⁴, and Z, provided that any O or S atom does not directly bond to another O or S atom, such that ring A is 13-32 membered; and where the alkylene or alkenylene chain contains 1 NR⁴COCOOR⁵ or NR⁴COCONR⁶R⁷, and where the alkylene or alkenylene chain contains 0-6 substituents selected from the group consisting of alkyl, hydroxy, alkoxy, and phenyl where the phenyl substituent is further substituted with 0-4 cyano, halo, alkyl, haloalkyl, alkoxy, or haloalkoxy substituents;
Ar¹ is phenyl, pyridinyl, pyrazolyl, isoxazolyl, isothiazolyl, imidazolyl, oxazolyl, thiazolyl, triazolyl, oxadiazolyl, or thiadiazolyl, and is substituted with 0-3 substituents selected from cyano, halo, alkyl, haloalkyl, hydroxy, alkoxy, or haloalkoxy;
X is O, CH₂, CO, CO₂, or C(O)NR⁴; and
Z is C₃₋₇ cycloalkylene, phenylene, pyrrolidindiyl, piperidindiyl, or piperazindiyl;
or a pharmaceutically acceptable salt thereof.
2. A compound of claim 1 where
a is C or N;
b is C or N;
R¹ is haloalkyl;
R² is hydrogen;
R⁴ is hydrogen or alkyl;
R⁵ is hydrogen or alkyl;
R⁶ is hydrogen, alkyl, (cycloalkyl)alkyl, (Ar¹)alkyl, cycloalkyl, (alkyl)cycloalkyl, tetralinyl, or Ar¹;
R⁷ is hydrogen or alkyl;
or R⁶ and R⁷ taken together with the nitrogen to which they are attached is azetidinyl, pyrrolidinyl, piperidinyl, piperazinyl, or morpholinyl, and is substituted with 0-3 substituents selected from hydroxyl, alkyl, alkylcarbonyl, and alkoxycarbonyl;
Q is an alkylene or alkenylene chain containing 2 groups selected from the group consisting of O and Z, provided that any O does not directly bond to another O atom, such that ring A is 13-32 membered; and where the alkylene or alkenylene chain contains 1 NR⁴COCOOR⁵ or NR⁴COCONR⁶R⁷;
Ar¹ is phenyl, isoxazolyl, thiazolyl, or thiadiazolyl, and is substituted with 0-3 substituents selected from cyano, halo, alkyl, haloalkyl, hydroxy, alkoxy, or haloalkoxy;
X is C(O)NR⁴; and
Z is phenylene;
or a pharmaceutically acceptable salt thereof.
3. A compound of claim 1 where a is N.
4. A compound of claim 1 where a is C.
5. A compound of claim 1 where b is C.
6. A compound of claim 1 where b is N.
7. A compound of claim 1 where Q is an alkylene or alkenylene chain containing 2 groups selected from the group consisting of O and Z, provided that any O does not directly bond to another O atom, such that ring A is 13-32 membered; and where the alkylene or alkenylene chain contains 1 NR⁴COCOOR⁵ or NR⁴COCONR⁶R⁷.
8. A compound of claim 1 where Q is an alkylene or alkenylene chain containing 1 O and 1 Z, such that ring A is 13-32 membered; and where the alkylene or alkenylene chain contains 1 NR⁴COCOOR⁵ or NR⁴COCONR⁶R⁷.
9. A compound of claim 8 where R⁴ is hydrogen or alkyl, R⁵ is hydrogen or alkyl, R⁶ is hydrogen, alkyl, (cycloalkyl)alkyl, (Ar¹)alkyl, cycloalkyl, (alkyl)cycloalkyl, tetralinyl, or Ar¹; R⁷ is hydrogen or alkyl; or R⁶ and R⁷ taken together with the nitrogen to which they are attached is azetidinyl, pyrrolidinyl, piperidinyl, piperazinyl, or morpholinyl, and is substituted with 0-3 substituents selected from alkyl, alkylcarbonyl, and alkoxycarbonyl.
10. A compound of claim 1 where Ar¹ is phenyl, isoxazolyl, thiazolyl, or thiadiazolyl, and is substituted with 0-3 substituents selected from cyano, halo, alkyl, haloalkyl, hydroxy, alkoxy, or haloalkoxy.
11. A compound of claim 1 where X is C(O)NR⁴.
12. A compound of claim 1 where Z is phenylene.
13. A compound of claim 1 selected from the group consisting of

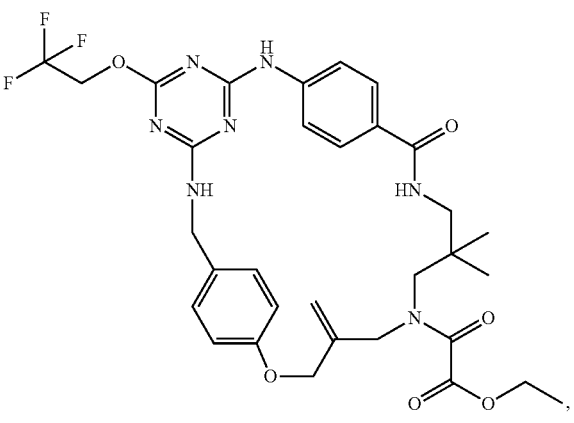

69
-continued
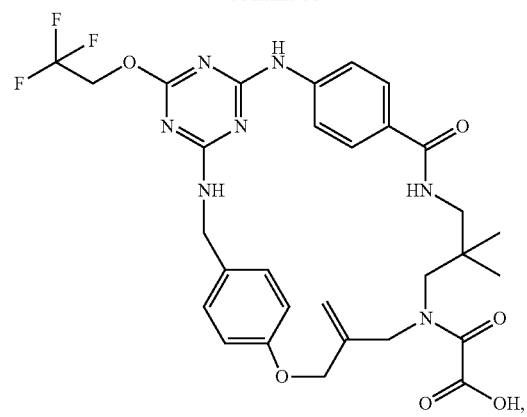
70
-continued
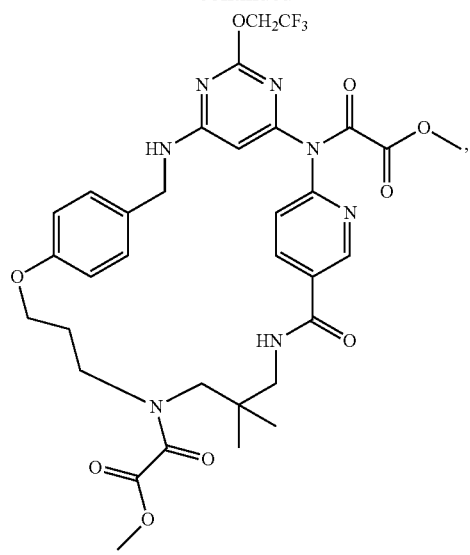
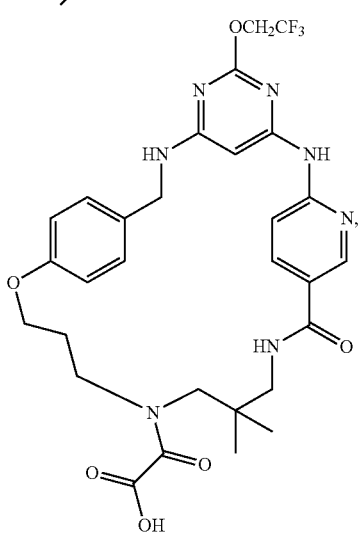
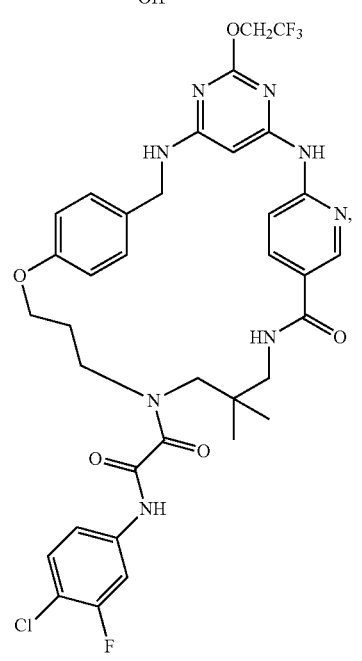

71
-continued
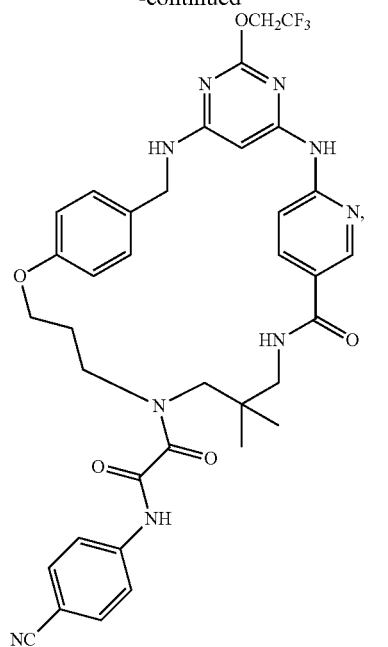
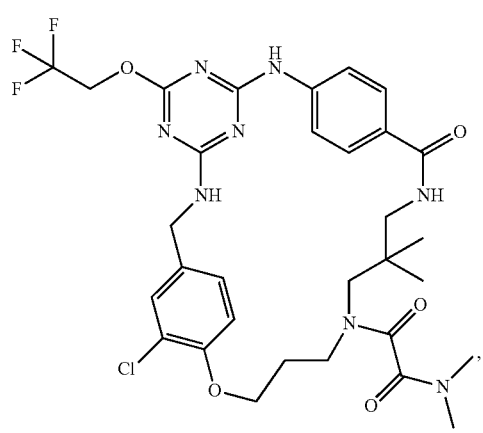
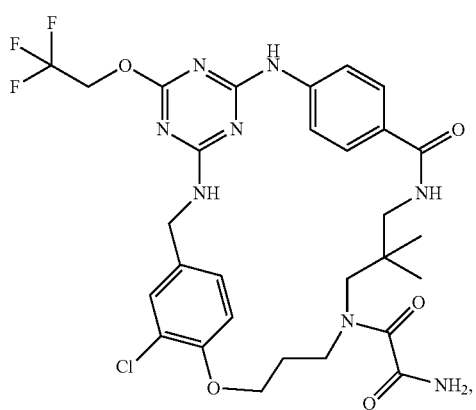
72
-continued
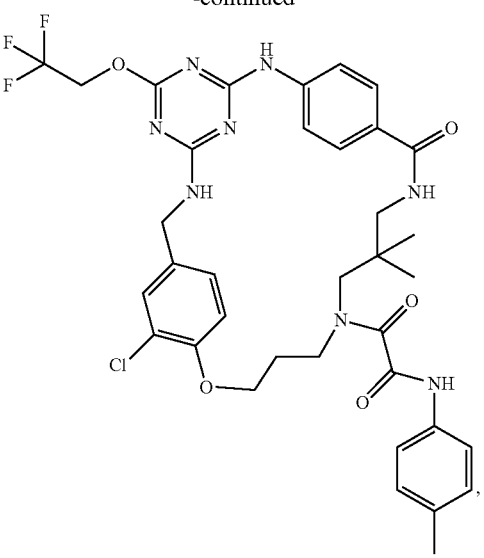
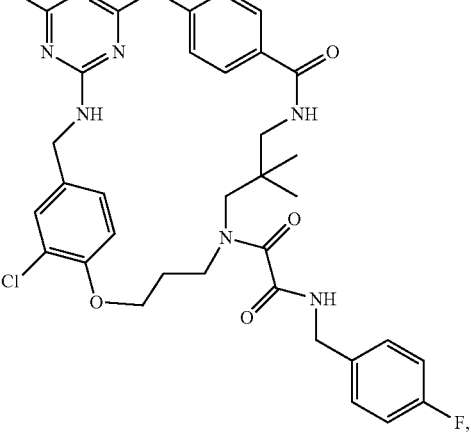

73
-continued
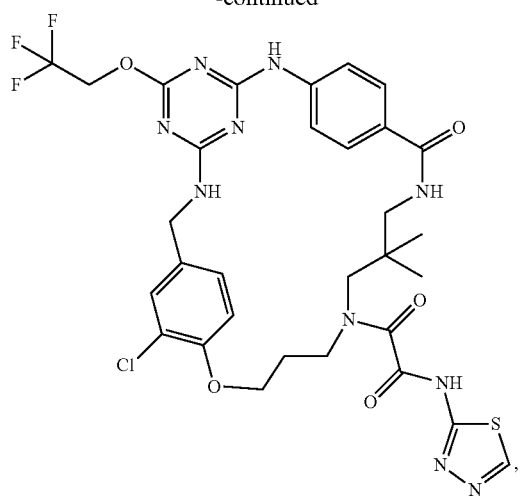
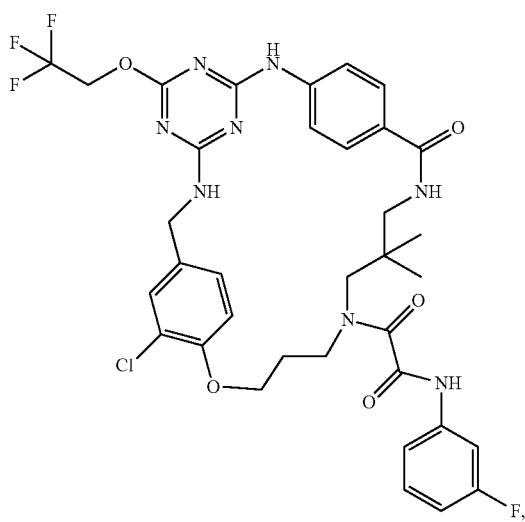
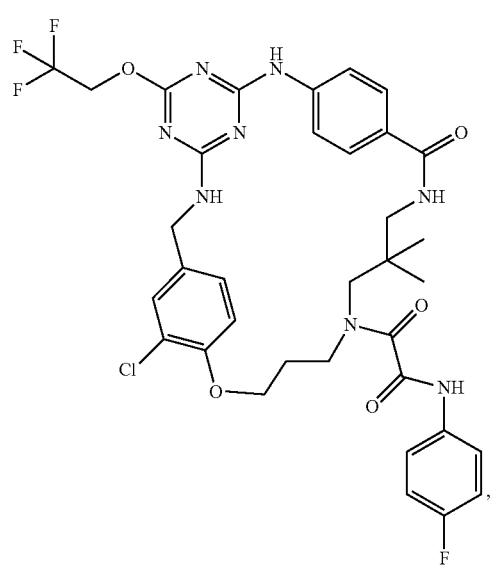
74
-continued
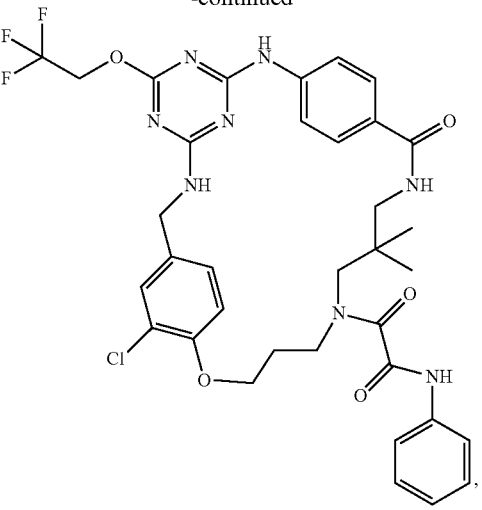
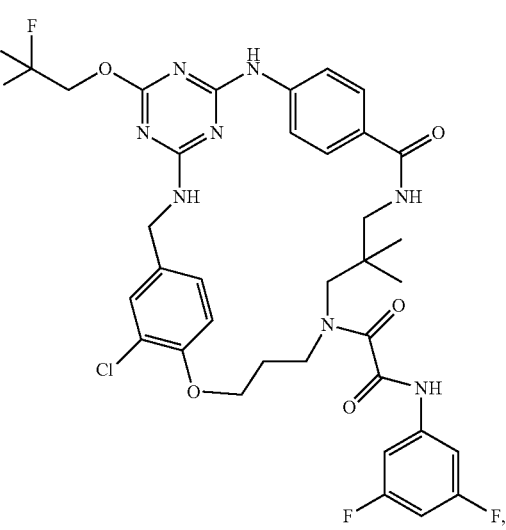

75
-continued
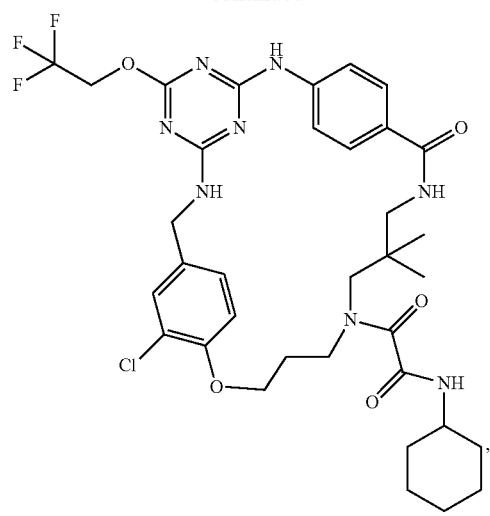
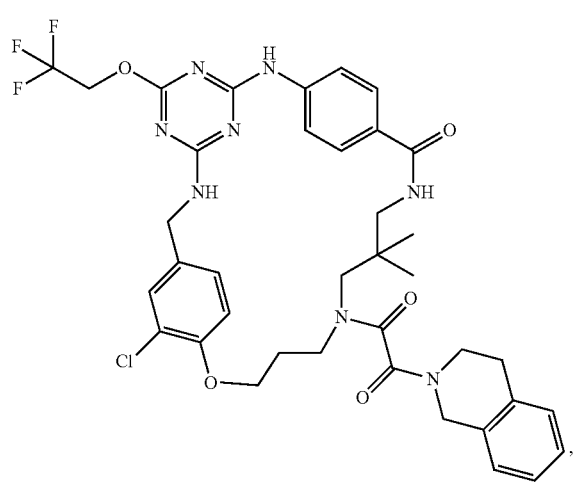
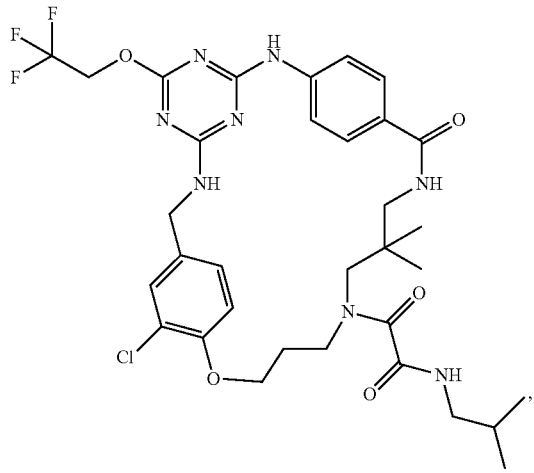
76
-continued
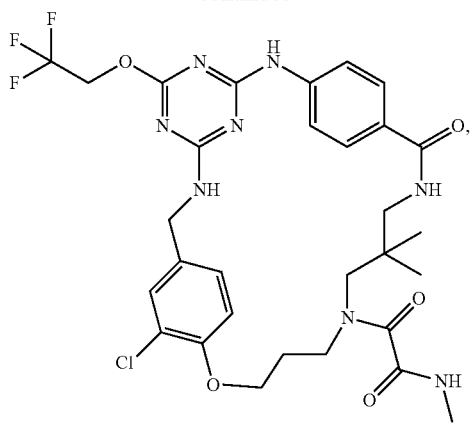
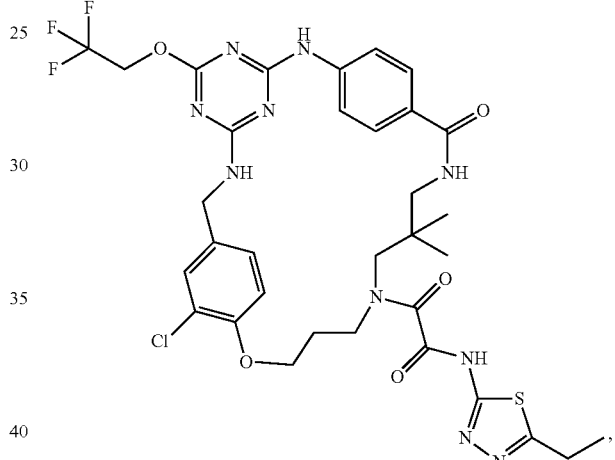
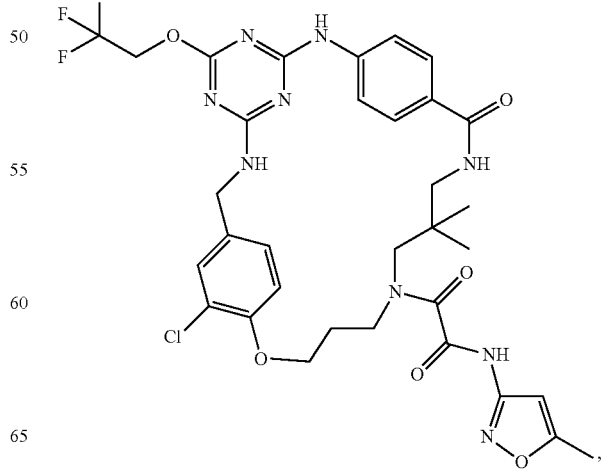

-continued
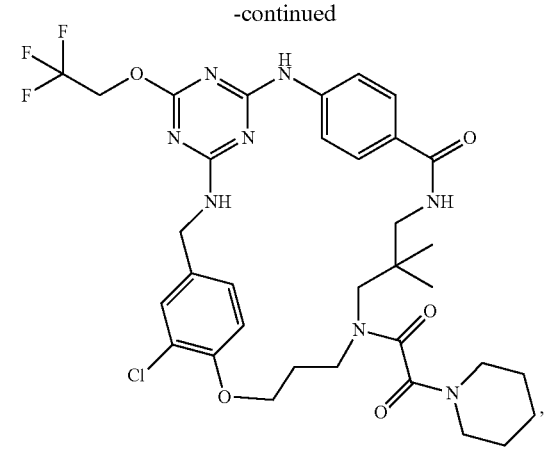
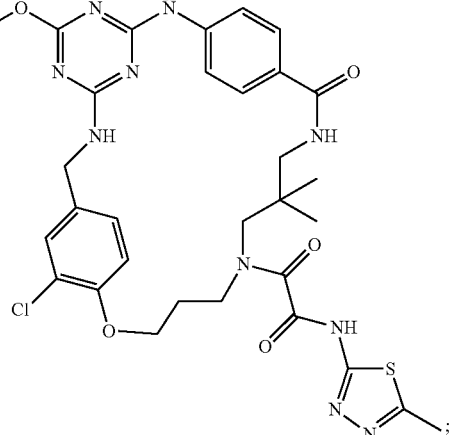
or a pharmaceutically acceptable salt thereof.
14. A composition comprising a compound of claim 1, or a pharmaceutically acceptable salt thereof, and a pharmaceutically acceptable carrier.
15. A method of treating hepatitis C infection comprising administering a therapeutically effective amount of a compound of claim 1 to a patient.
* * * * *